United States Patent [19]

Godfrey

[11] Patent Number: 4,801,366
[45] Date of Patent: Jan. 31, 1989

[54] APPARATUSES AND METHODS FOR ANALYZING MACRO-IONS AT ELECTROPHORETIC STEADY STATE

[76] Inventor: Jamie E. Godfrey, 2559 Steele Rd., Baltimore, Md. 21209

[21] Appl. No.: 27,538

[22] Filed: Mar. 18, 1987

[51] Int. Cl.[4] .................. G01N 27/26; G01N 27/28
[52] U.S. Cl. ........................ 204/180.1; 204/301; 204/182.3; 356/344
[58] Field of Search ............... 356/344, 36; 204/180.1, 204/182.3, 299 R, 301

[56] References Cited

U.S. PATENT DOCUMENTS

| | | | |
|---|---|---|---|
| 956,246 | 4/1910 | White et al. | 426/241 |
| 1,235,063 | 7/1917 | Schwerin | 204/182.4 |
| 1,815,302 | 7/1931 | Hogstad | 204/131 |
| 2,219,209 | 10/1940 | Neufeld | 204/182.3 |
| 2,251,082 | 7/1941 | Theorell | 204/182.3 |
| 2,412,602 | 12/1946 | Chambers et al. | 356/344 |
| 2,878,178 | 3/1959 | Bier | 204/182.3 |
| 3,079,318 | 2/1963 | Bier | 204/182.3 |
| 3,320,149 | 5/1967 | Isreeli | 204/299 R |
| 3,346,479 | 10/1967 | Natelson . | |
| 3,384,564 | 5/1968 | Ornstein et al. . | |
| 3,450,624 | 6/1969 | Natelson . | |
| 3,498,905 | 3/1970 | Strickler . | |
| 3,668,107 | 6/1972 | Lappe . | |
| 3,697,406 | 10/1972 | Svendsen . | |
| 3,720,593 | 3/1973 | Juhos | 204/299 R |
| 3,747,024 | 7/1973 | Gordon et al. | 204/299 R |
| 3,839,175 | 10/1974 | Keyes . | |
| 3,855,111 | 12/1974 | Allington . | |
| 3,871,990 | 3/1975 | Hadermann et al. . | |
| 4,164,464 | 8/1979 | Allington et al. . | |
| 4,515,676 | 5/1985 | Kawai et al. | 204/299 R |
| 4,617,104 | 10/1986 | Kawai et al. | 204/299 R |

FOREIGN PATENT DOCUMENTS 242358 10/1962 Australia .................. 204/299 R

OTHER PUBLICATIONS

"Diffusion Osmotic Equilibrium", authored by Alfred Polson and published in the Biochimica Et Biophysica Acta, 43 (1960), pp. 145–151.

Primary Examiner—John F. Niebling
Assistant Examiner—John S. Starsiak, Jr.

[57] ABSTRACT

A stable, unchanging concentration gradient of macro-ions dissolved in aqueous or other polar solvents is established adjacent to a semipermeable membrane by the opposing forces of a directed electric field and diffusion, a condition herein defined as electrophoretic steady state. An analysis of the concentration gradient as recorded by an interrogating optical system can yield one or more physical-chemical properties of the macro-ions.

10 Claims, 12 Drawing Sheets

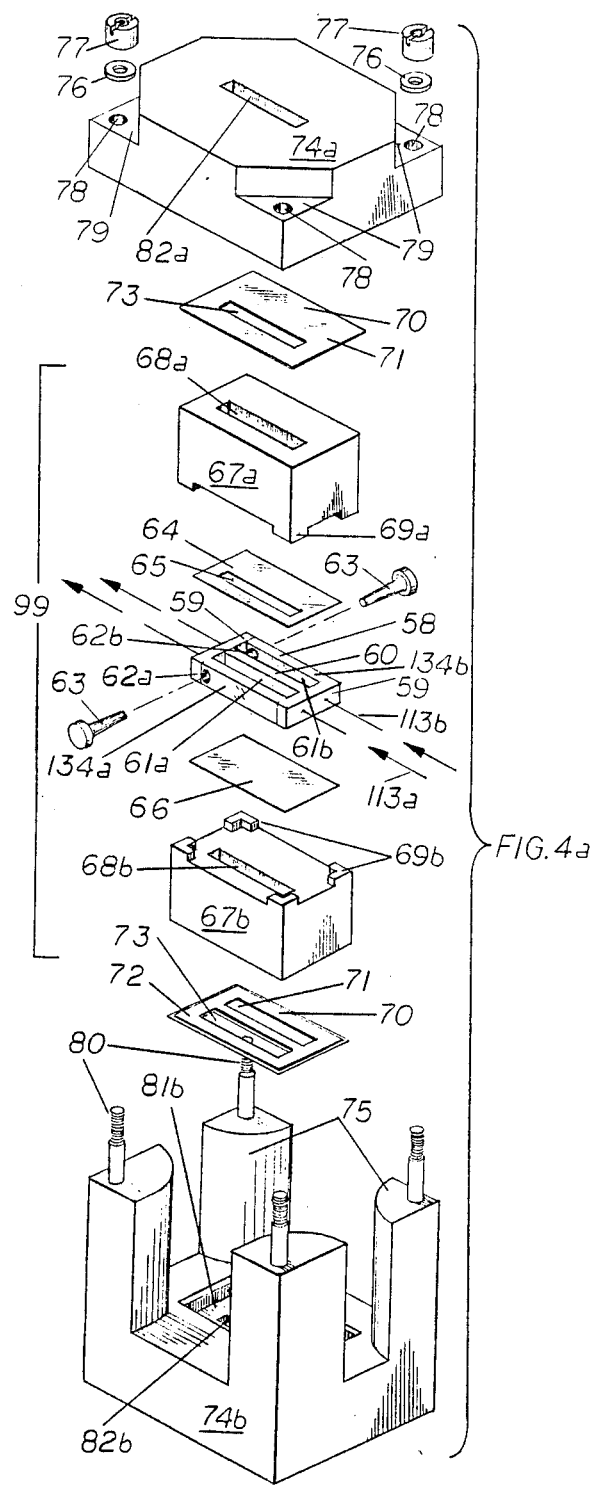

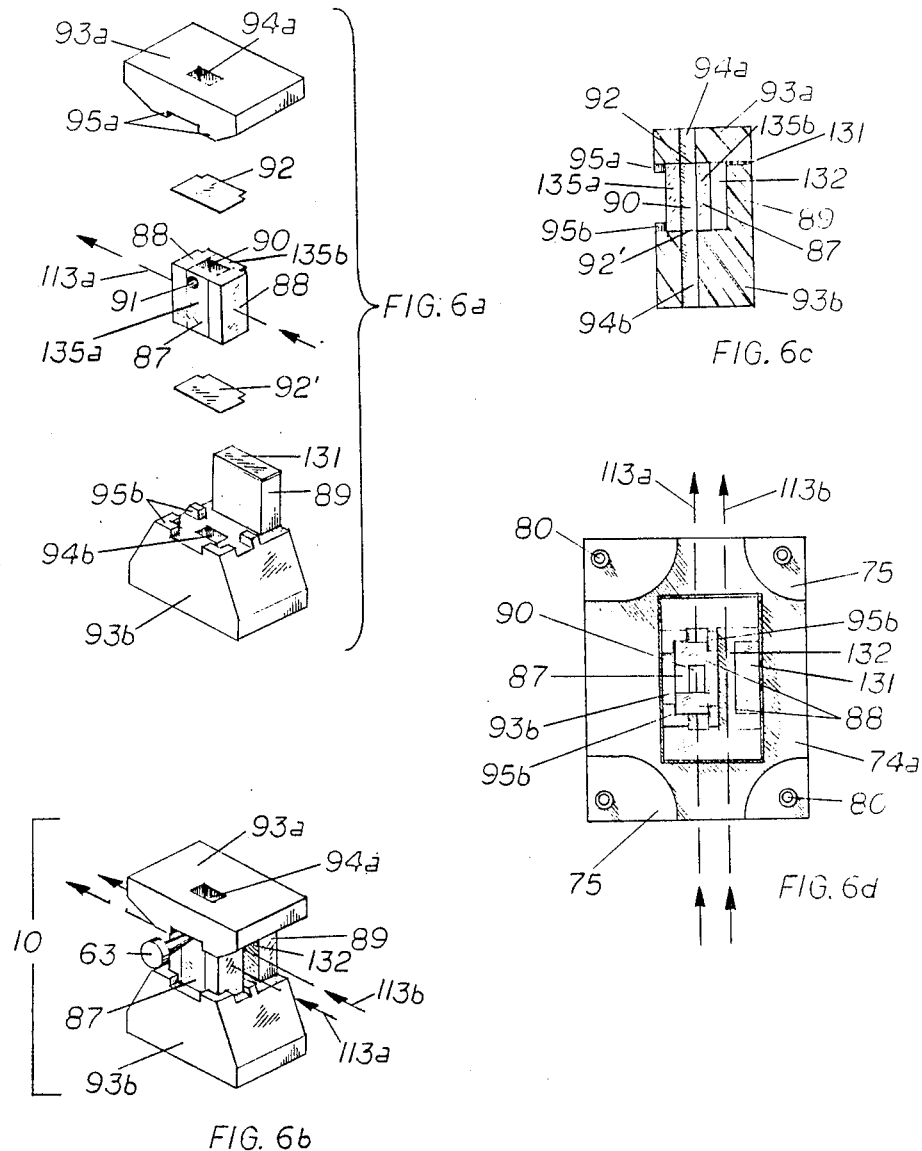

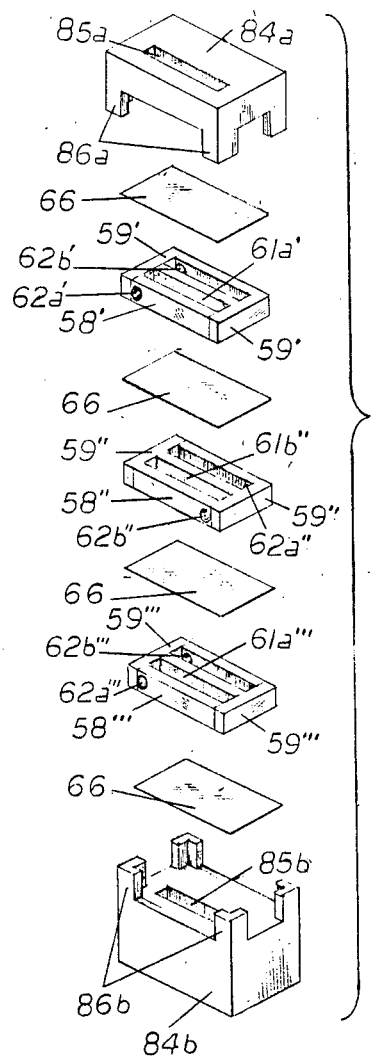
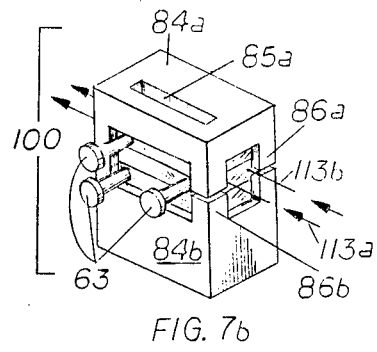
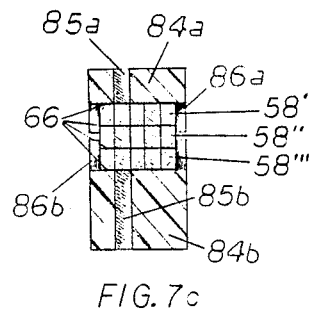

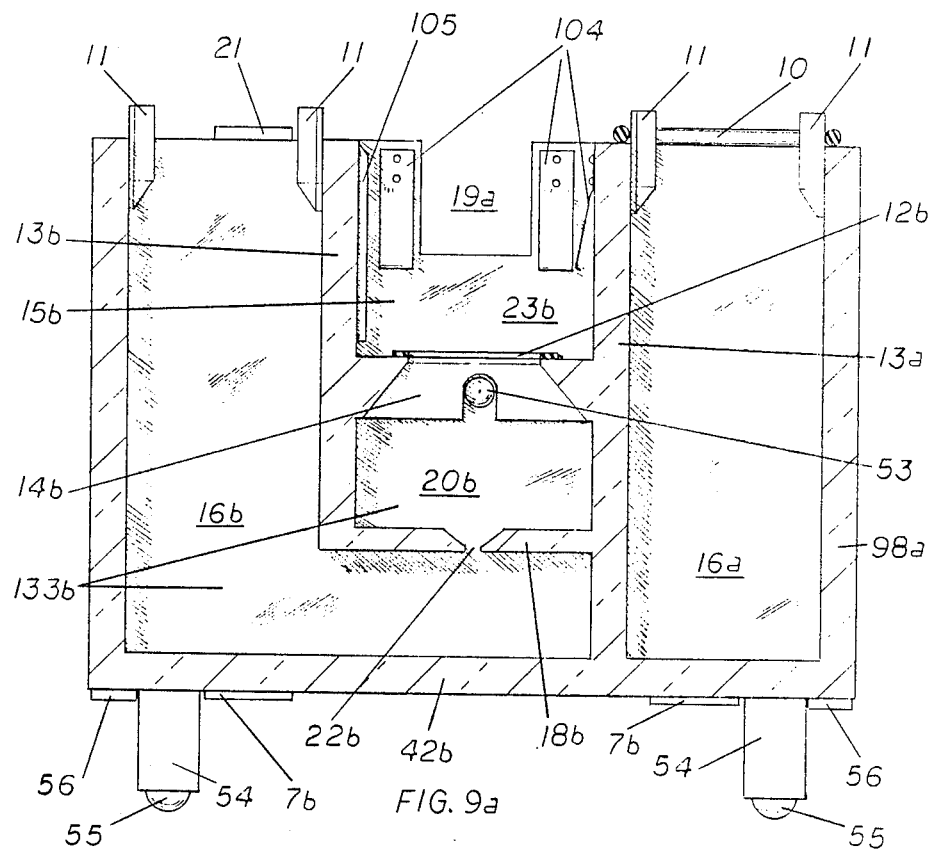
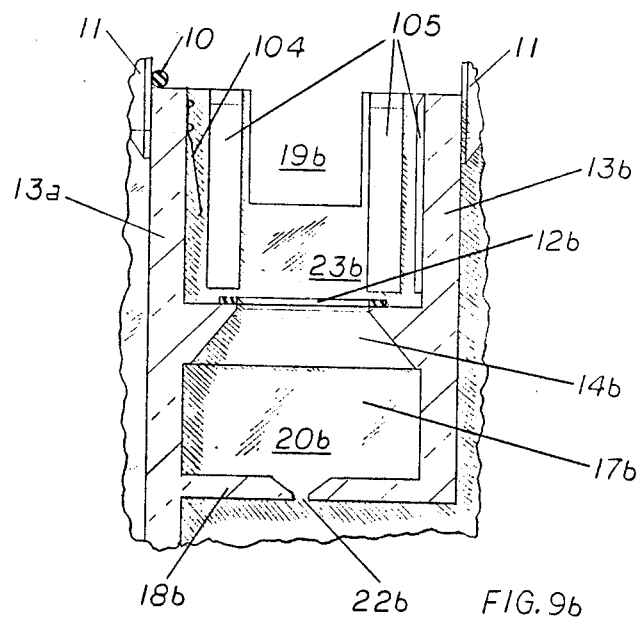

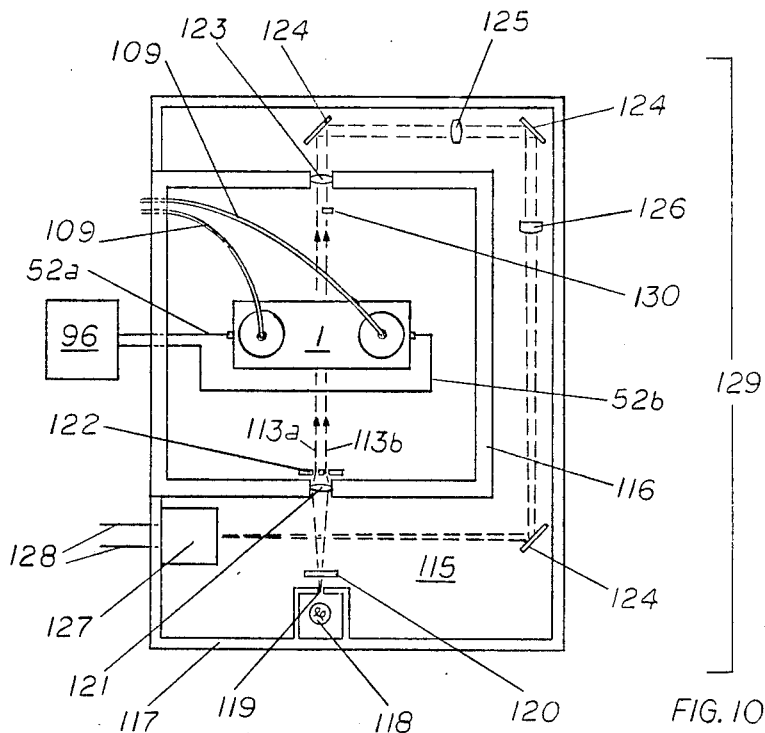
FIG. 10
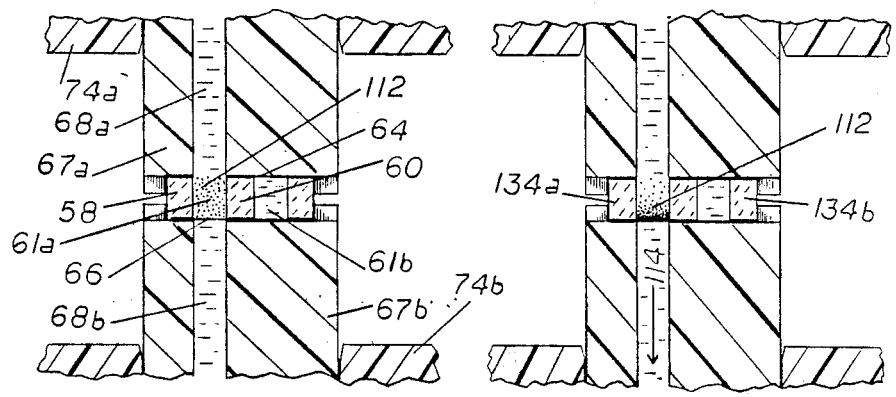
FIG. 11a
FIG. 11b
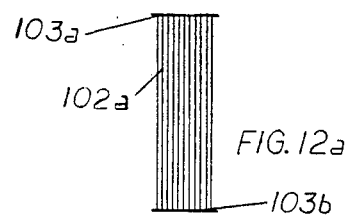
FIG. 12a
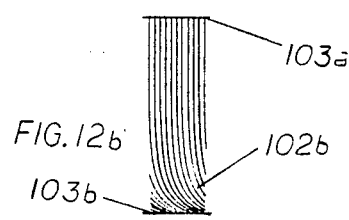
FIG. 12b

APPARATUSES AND METHODS FOR ANALYZING MACRO-IONS AT ELECTROPHORETIC STEADY STATE

BACKGROUND OF THE INVENTION

The present invention relates to the measurement of physical-chemical properties of macromolecules. More specifically, it pertains to apparatuses and methods for (1) establishing and maintaining macro-ions (e.g., proteins) dissolved in aqueous and other polar solvents at electrophoretic steady state (defined below) under well-characterized conditions and (2) facilitating the precise and quantitative optical interrogation of the macro-ions so maintained. Analyses of the optical records of macro-ions maintained at electrophoretic steady state in accordance with the apparatuses and methods of the present invention can yield one or more physical-chemical properties of the macro-ions including molar diminished charges (defined below), stoichiometries of assembly and association constants of reversibly associating macro-ion systems, and polydispersity parameters of mixtures of homologous macro-ions (e.g., a production run of a synthetic, linear, charge-bearing polymer). The aforesaid analyses are based on electrophoretic steady-state theory, developed by the inventor and described publicly for the first time in this disclosure.

Because the present invention provides for the first time apparatuses and methods for analyzing macro-ions at electrophoretic steady state, there is no directly related prior art with which the present invention can be compared. Thus, prior electrophoretic techniques, as for example the prior techniques of moving boundary electrophoresis and zonal electrophoresis both of which are based on established electrophoretic transport theory, differ fundamentally from the present invention, as do methods and apparatuses of the prior technique of isoelectric focusing.

However, the technique of steady-state electrophoresis—the term referring here and often throughout this disclosure to the technique of measuring physical-chemical properties of macro-ions maintained at electrophoretic steady state in accordance with the apparatuses and methods of the present invention—can be classified with prior analytical techniques employed to make precise measurements of physical-chemical properties of macromolecules maintaind at chemical or quasi-chemical equilibrium. Several of these prior techniques including the techniques of osmotic pressure, light scattering, and equilibrium ultracentrifugation measure one or more of the properties measured by the steady-state electrophoresis technique. This class of techniques is sometimes favorably compared with hydrodynamic techniques, which include the prior electrophoretic transport techniques alluded to above, whose theoretical bases are, in general, more empirical and model-dependent than the theoretical bases of the chemical-quasi/chemical-equilibrium techniques (see for instance, Cantor, C. R., & Schimmel, P. R. (1980), *Biological Chemistry, Part II: Techniques for the Study of Biological Structure and Function*, San Francisco, CA, W. H. Freeman and Co.)

The prior chemical-equilibrium techniques of osmotic pressure and light scattering have only occasionally been used to characterize reversibly associating macromolecular systems since these techniques make only a single molecular-weight measurement per experiment and the analysis of reversibly associating systems require many molecular-weight estimates over an often large concentration span. Moreover, because each of these prior techniques measures only one molecular-weight moment, neither is appropriate for estimating dispersity parameters of mixtures of homologous macromolecules.

The prior technique of equilibrium ultracentrifugation, however, has often been utilized to analyze both reversibly associating macromolecular systems and mixtures of homologous macromolecules. A single equilibrium ultracentrifugation analysis carried out in the analytical ultracentrifuge generates effective reduced molecular weights over a large interval of macromolecular concentration. Moreover, both the apparent weight- and z-average effective reduced molecular-weight moments can be determined throughout the macromolecular concentration span generated in the analytical ultracentrifuge at sedimentation equilibrium, and under conditions of meniscus depletion, the apparent number-average effective reduced molecular weight can be calculated as well. Generally in equilibrium ultracentrifugation analyses, effective reduced molecular weights are converted to absolute molecular weights by appropriate conversion factors; however, for the purpose of characterizing reversibly associating macromolecular systems and mixtures of homologous macromolecules, effective reduced molecular weights may be employed with substantially equal facility (the relationship between effective reduced and absolute molecular weights in equilibrium ultracentrifugation theory can be found in Yphantis, D. A., *Equilibrium Ultracentrifugation of Dilute Solutions*, Biochemistry, 3 (1964), 297; see also below). The capacity to measure more than one moment of apparent effective reduced molecular weight makes the prior technique of equilibrium ultracentrifugation particularly suitable for analyzing mixtures of homologous macromolecules; and the large span of macromolecular concentration over which effective reduced molecular weights may be measured in one analysis especially lends the prior technique of equilibrium ultracentrifugation to the study of reversibly associating macromolecular systems.

The prior theory of equilibrium ultracentrifugation has many formal parallels with the theory of steady-state electrophoresis upon which the methods and designs of the apparatuses of the present invention are based (see below). In addition, the measurements made by the prior technique of equilibrium ultracentrifugation and the technique of steady-state electrophoresis overlap to a large degree. Accordingly, the technique of steady-state electrophoresis possesses many of the advantages associated with the prior technique of equilibrium ultracentrifugation enumerated above. Thus, although electrophoretic, the technique of steady-state electrophoresis is most similar to the prior technique of equilibrium ultracentrifugation, and the methods and apparatuses of the prior technique of equilibrium ultracentrifugation are the prior art with which the present invention is most appropriately compared.

Despite many favorable features, however, the prior technique of equilibrium ultracentrifugation suffers from a number of disadvantages which relate primarily to technical and practical limitations of the analytical ultracentrifuge in which equilibrium ultracentrifugation analyses are performed. Several principal disadvantages of the analytical ultracentrifuge (as exemplified by the Model E Analytical Ultracentrifuge, Beckman Instruments, Palo Alto, CA) relate to the inherent technical difficulties of measuring macromolecular concentration gradients stabilized at sedimentation equilibrium: First, the cells containing stabilized macromolecular concentration gradients at sedimentation equilibrium are fitted to a spinning rotor; consequently, the cells are aligned only for a small fraction of the time in the instrument's optical systems. The resultant low light levels create unfavorable signal-to-noise ratios in the images of the macromolecular concentration gradients recorded by the absorption system. In addition, despite the employment of powerful light sources (including lasers in some custom installations) in the Rayleigh interference optical system, a highly sensitive ("grainy") photographic emulsion is required to record interferograms of the gradients; this high sensitivity is gained at the expense of optical resolving power.

Second, most studies by the prior technique of equilibrium ultracentrifugation are conducted at rotor speeds which cause significant optical distortions in the cell windows, even when sapphire windows (intended for high rotor speeds) are used. These distortions can create optical transmission irregularities, especially at the low wavelengths often used with the absorption optical system; they can also cause reductions in the clarity and warping of Rayleigh interferograms. Moreover, optical defects introduced into the cell windows during equilibrium ultracentrifugation analyses of macromolecules are not always precisely duplicated in the solvent (blank) analyses, which by subtraction are designed to eliminate the effects of distortions in the optical systems during the processing of equilibrium ultracentrifugation data.

Third, Rayleigh interference patterns (interferograms) are produced in the ultracentrifuge only when the two cell-window slits of the cell in the spinning rotor align with the two slits of the double-slit interference mask; during each revolution of the rotor, however, each cell-window slit is aligned once with the "wrong" slit of the interference mask resulting in undiffracted light superimposing on the interference patterns. This contaminating light (approximately half of the light reaching the photographic plate) significantly reduces the contrast and clarity of the interferograms. The contaminating light and the "graininess" of the photographic image discussed above have been contributing factors to the only marginal success to date of incorporating advanced techniques into the analysis of Rayleigh interferograms generated in the analytical ultracentrifuge (e.g., by the application of automated image-analysis techniques in the recording of interferograms). Consequently, photographic records of interferograms are routinely measured manually on an optical micro-comparator; even when the micro-comparator is equipped to automatically transmit the x-y coordinates of interferograms to a computer, the complete analysis of the data from a typical equilibrium ultracentrifugation experiment can consume several hours.

Most importantly, these aforesaid factors which reduce the capacities of the optical systems of the analytical ultracentrifuge to faithfully record concentration gradients in cells at sedimentation equilibrium introduce often unacceptable levels of random and instrumental error into the data. The result has been failure in attempts to unambiguously characterize several reversibly self-associating protein systems by the prior technique of equilibrium ultracentrifugation and the generation of undesirably low confidence levels in the estimates of polydispersity parameters of mixtures of homologous macromolecules.

The analytical ultracentrifuge possesses other disadvantages of a more practical nature. Its physical dimensions require a large area of often scarce laboratory space; its weight and sensitivity to external vibrations require it to be supported on a stable, heavy-load-bearing floor. Several features make the instrument hazardous to use: for instance, the high-voltage, water-cooled light source of the Rayleigh interference optical system presents a major electrical shock hazard, and when operated at high speeds, the heavy titanium rotors often employed in the instrument possess sufficient kinetic energy to break through the steel barrier which surrounds the rotor chamber if the drive motor, drive shaft, or rotor, itself, should fail.

A principal disadvantage of the analytical ultracentrifuge is its initial price and the cost of maintenance, parts replacement, and repair, which are among the highest for a commercial, widely marketed instrument. The high initial price reflects the materials and design requirements of a device which must withstand large physical stresses, and the high maintenance, repair, and parts-replacement costs are a consequence of the wear and fatigue which these stresses impose on many components. For an analytical ultracentrifuge in routine use, the rotor drive is replaced as frequently as twice a year; cells exposed to high rotor speeds can fail after several months.

The molar diminished charge is one property of macro-ions measured in the apparatuses of the present invention by the technique of steady-state electrophoresis which can not be measured by any prior chemical-/quasichemical-equilibrium technique, including the prior technique of equilibrium ultracentrifugation. This property—which can be defined approximately as the apparent (decreased) charge carried by an ion as a result of interactions between it and other ions present in solution—is a quantity of particular interest to the polyelectrolyte chemist. Currently, molar diminished charges of macro-ions are estimated by prior electrophoretic transport techniques, including the prior technique of moving boundary electrophoresis. However, these prior techniques are only capable of estimating molar diminished charges of macro-ions whose frictional coefficients have been experimentally established (sometimes a difficult procedure) or calculated on the basis of assumptions concerning the shapes and sizes of the macro-ions.

SUMMARY OF THE INVENTION

A principal object of my invention is to provide apparatuses and methods for establishing and maintaining macro-ions dissolved in aqueous and other polar solvents in well-defined, substantially stable—i.e., substantially static and substantially unchanging—concentration gradients by the opposing forces of diffusion and an externally imposed, directed electrical field; macro-ion concentration gradients so established and maintained are described in this disclosure as being under conditions of electrophoretic steady state. Each concentration gradient of macro-ions maintained at electrophoretic steady state within the apparatuses of the present invention is established against a semipermeable membrane toward which the macro-ions are driven by a directed electrical field. The directed electrical field is supported by small ions, typically inorganic ion, which are an essential component of the solvent and which can pass through the semipermeable membranes fitted to the apparatuses of the present invention; said semipermeable membranes are impermeable, however, to the much larger macro-ions. The directed electrical field is maintained at a value such that the diffusion of macro-ions away from each semipermeable membrane (generated by the concentration gradient of said macro-ions which forms at each semipermeable membrane surface) and the directed electrical field establish the stable macro-ion concentration gradient with dimensions suitable for precise, quantitative analyses.

Another principal object of my invention is to provide apparatuses and methods for establishing well-defined and highly uniform directed electrical fields for the purpose of establishing and maintaining macro-ions at electrophoretic steady state when an electrical potential difference is applied across the electrodes of the apparatuses by a direct-current, continuously adjustable, electrical power source external to the apparatuses of the present invention. To within experimentally insignificant tolerances, the directed electrical fields are linear throughout the volume of solution occupied by each macro-ion ion sample established at electrophoretic steady state. Moreover, to within experimentally insignificant tolerances, the directed electrical fields are perpendicular to each semipermeable membrane surface, over the entire surface of the semipermeable membrane, against which macro-ions are maintained at electrophoretic steady state. These features ensure that the macro-ion concentration gradients established at electrophoretic steady state in the apparatuses of the present invention are also well-defined and highly uniform; i.e., each lamella of macro-ion solution within said gradients parallel to the semipermeable membrane surfaces is of substantially uniform chemical composition throughout.

Another principal object of my invention is to provide apparatuses and methods for facilitating the quantitative optical interrogation of macro-ions maintained at electrophoretic steady state. Each macro-ion concentration gradient established at electrophoretic steady state against an aforesaid semipermeable membrane is enclosed within the interrogation chamber of a single-chamber rectangular interrogation cell or within one interrogation chamber of a double-chamber rectangular interrogation cell. The interrogation chambers are partially bounded by vertical parallel walls. Two of the walls, disposed oppositely, are optically true windows which function as optical energy entry and exit ports. The ports allow the interrogation chamber(s) to be conveniently interrogated by either single-beam or dual-beam optical systems which are capable of measuring the concentrations of macromolecules dissolved in aqueous or other polar solvents. Principal examples of such optical systems include Rayleigh interference optical systems and single- and dual-beam absorption optical systems. The design of the apparatuses of the present invention allows an aforesaid interrogating optical system to generate optical records of macro-ion concentration gradients maintained at electrophoretic steady state within the apparatuses of the present invention which yield precise, quantitative descriptions of said gradients. Moreover, the designs of the interrogation cells and other apparatuses of the present invention and specifically the dimensions of the single- and double-chamber interrogation cells are compatible with dimensional specifications of the beams of optical energy of Rayleigh interference and single- and dual-beam absorption optical systems currently incorporated into many research instruments for the purpose of interrogating solutions of macro-molecules.

Although the aforesaid concentration gradients of macro-ions maintained at electrophoretic steady state within the apparatuses of the present invention are of diminutive dimensions (typically less than 4 mm in extent along the axis of the gradient), precise analyses of the aforesaid optical records of said gradients following procedures defined by electrophoretic steady-state theory yield one or more physical-chemical properties of the macro-ions. Another principal object of the present invention, therefore, is to provide apparatuses and methods for facilitating the measurement of physical-chemical properties of macro-ions dissolved in aqueous or other polar solvents by the new analytical technique of steady-state electrophoresis. It is contemplated that the apparatuses of the present invention will be incorporated into an instrument assembly which will also include an aforementioned optical system and an aforementioned electrical power source among its principal components. The instrument assembly would be employed in carrying out electrophoretic steady-state analyses on macro-ion samples which would yield physical-chemical measurements of scientific and technical importance.

Another object of my invention is to provide apparatuses and methods for establishing and maintaining macro-ions at electrophoretic steady state which permit flexibility with regard to analytical conditions, including (1) the number of interrogation cells fitted to the apparatuses during an electrophoretic steady-state analysis; (2) the lengths of the optical paths and heights (dimension parallel to the directed electrical field) of the interrogation cell(s) fitted to the apparatuses; (3) the type of interrogation cell(s), i.e., single- or double-chamber, fitted to the apparatuses, a choice determined by the requirements of the optical system employed to interrogate the macro-ions maintained at electrophoretic steady state; and (4) the geometry of the macro-ion concentration gradients maintained at electrophoretic steady state within the apparatuses. With reference to the last-mentioned analytical condition, both partial and complete macro-ion concentration gradients may be maintained at electrophoretic steady state within the apparatuses of the present invention. Complete macro-ion concentration gradients approach infinite dilution within the interrogation cells in which they are enclosed (i.e., at a point distal to the semipermeable membrane against which said gradients are formed). Partial macro-ion concentration gradients are delimited at their more dilute ends by semipermeable membranes which prevent the macro-ions of said gradient from diffusing further to infinite dilution; the resulting "truncated" concentration gradients are thus partially bounded between two semipermeable membranes. The available choices among the above analytical conditions are made possible by the inclusion in the present invention of several interrogation cell subassemblies of different design, each of which can be fitted to the appropriate apparatuses of the present invention.

Another object of my invention is to provide apparatuses and methods for establishing and maintaining macro-ions at electrophoretic steady state which permit macro-ion samples to be introduced and removed from the apparatuses after the said apparatuses have been charged with solvent and are otherwise operational. This feature of the present invention can greatly reduce the turnaround between successive electrophoretic steady-state analyses.

Another object of my invention is to provide apparatuses and methods for establishing and maintaining macro-ion concentration gradients, stabilized at electrophoretic steady state, with density gradients of said gradients directed downward in order to minimize the potentially destabilizing effects of density inversions on said gradients. Because the density and concentration vectors of the majority of macro-ion gradients established in aqueous solution are directionally the same, macro-ion concentration gradients are typically established at electrophoretic steady state against the upper surfaces of horizontally disposed semipermeable membranes fitted to the apparatuses of the present invention. However, means are also provided in the present invention for establishing macro-ion concentration gradients stabilized at electrophoretic steady state against the lower surfaces of horizontally disposed semipermeable membranes to properly accommodate those (rare) macro-ion gradients whose concentration and density vectors are directionally opposed.

Another object of my invention is to provide apparatuses and methods for neutralizing the potentially destabilizing effects of osmotic pressure on macro-ion concentration gradients established and maintained at electrophoretic steady state within the apparatuses of the present invention. During the operation of the apparatuses of the present invention, macro-ions are present at a higher concentration on one side of each semipermeable membrane fitted to the apparatuses than on the other; often one side of each semipermeable membrane is in contact with solvent only. The osmotic pressure this condition generates can cause bulk solvent flow across the semipermeable membranes which can disrupt the stability of the macro-ion concentration gradients. The apparatuses of the present invention are designed to permit a differential hydrostatic pressure to be applied across the semipermeable membranes (whenever it is necessary) to reduce the aforesaid solvent flow to experimentally insignificant rates.

Another object of my invention is to provide apparatuses and methods for establishing and maintaining macro-ions at electrophoretic steady state which permit potentially corrosive gases generated at the electrodes of the apparatuses of the present invention during their operation to be vented to the outside of the aforementioned instrument assembly of which the apparatuses are contemplated to be an integral component.

Each macro-ion concentration gradient established within the apparatuses of the present invention at electrophoretic steady state is contained within a stationary optical silica interrogation cell which can be continuously aligned in an optical system of choice. Consequently, both absorption and Rayleigh interference images of macro-ion concentration gradients established at electrophoretic steady state in the apparatuses of the present invention are more intense and of much higher optical quality than their counterparts obtained from the analytical ultracentrifuge during a typical analysis by the prior technique of equilibrium ultracentrifugation. Equally important, Rayleigh interference patterns of macro-ions established at electrophoretic steady state in the apparatuses of the present invention, unlike those obtained from the aforesaid prior art, are substantially uncontaminated by undiffracted light. Moreover, nonreproducible optical distortions, such as those often imparted by strong centrifugal fields into the windows of analytical ultracentrifuge cells, are substantially absent from the windows of the interrogation cells of the apparatuses of the present invention during an electrophoretic steady-state analysis; accordingly, the solvent (blank) analyses carried out in the apparatuses of the present invention (see below) can more completely eliminate by subtraction the effects of the inherent optical imperfections of the optical system employed to interrogate macro-ions established at electrophoretic steady state within the apparatuses of the present invention. The resultant lower instrumental error present in the optical data obtained from the apparatuses of the present invention and the higher precision of the optical data permit more precise analyses of macro-ion concentration gradients estalished in the apparatuses of the present invention than are possible of comparable macromolecular gradients generated in the aforesaid prior art. This contrast in precision is most dramatically seen in the analyses of data from the low-concentration ends of macromolecular gradients generated in the apparatuses of the present invention and the aforesaid prior art.

As a direct consequence of the high precision capabilities of the present invention, it is contemplated that: (1) the analyses of reversibly mixed- and self-associating macro-ion systems brought to electrophoretic steady state in the apparatuses of the present invention will yield more accurate stoichiometries of assembly and association constants than can be obtained currently by the prior technique of equilibrium ultracentrifugation; and (2) analyses of mixtures of homologous macro-ions brought to electrophoretic steady state in the apparatuses of the present invention will provide more accurate estimates of polydispersity parameters (e.g., weight-to-number-average molecular-weight ratios) than can be determined from the aforesaid prior art.

Analyses of the concentration gradients of macro-ions maintained at electrophoretic steady state in the apparatuses of the present invention also yield molar diminished charges of the macro-ions, quantities currently measured by prior electrophoretic transport techniques. However, unlike said prior techniques, the technique of steady-state electrophoresis carried out in the apparatuses of the present invention is capable of measuring molar diminished charges of macro-ions whose frictional coefficients have not been determined and can not be estimated with confidence. The present invention, therefore, fulfills a long-standing need in an important area of research.

It is further contemplated that the superior optical quality of the interference patterns (generated by an interrogating Rayleigh interference optical system) which can be obtained of macro-ion concentration gradients generated in the apparatuses of the present invention will allow said patterns to be recorded by automated image-analysis techniques currently employed, for instance, in the analysis of stained electrophoresis slab gels. Digital descriptions of the Rayleigh interference patterns could be fed directly into a computer for additional analysis. These automated procedures would obviate the need for manual analyses of the photographic records of the Rayleigh interference patterns on an optical micro-comparator, as is routinely required in the processing of similar interference patterns encountered in the prior art of equilibrium ultracentrifugation. In this regard, it should be noted that attempts to digitize interferograms of macromolecules maintained at sedimentation equilibrium in the analytical ultracentrifuge have met with marginal success. It is reasonable to surmise, therefore, that the significantly higher quality interferograms which can be obtained of macro-ion concentration gradients maintained at electrophoretic steady state in the apparatuses of the present invention will be much more successful cndidates for this automation process.

It is also contemplated that the absorption images (generated by an interrogating single- or dual-beam absorption optical system) obtained of macro-ion concentration gradients produced in the apparatuses of the present invention will be analyzed by automated image-analysis techniques as well. Although macromolecular concentration gradients established in the analytical ultracentrifuge during analyses by the prior technique of equilibrium ultracentrifugation are currently recorded by automated techniques, the enhanced intensity and optical quality of the absorption images obtained of macro-ion concentration gradients maintained at electrophoretic steady state in the apparatuses of the present invention should permit the generation of data possessing much more favorable signal-to-noise ratios than are typically produced in the aforesaid prior art.

In addition to the apparatuses of the present invention, a complete instrument assembly for making measurements on macro-ions at electrophoretic steady state would include one or more optical interrogation systems, a direct-current, continuously adjustable electrical power source, a thermostatted housing, a refrigeration unit, and image analyzing assemblies among its principal components. The modest size of the preferred embodiment of the present invention would permit its incorporation into a complete instrument assembly of sufficiently compact dimensions as to be easily accommodated on the typical laboratory bench top; moreover, said instrument assembly's sensitivity to vibration would be no more than average for a precision instrument. The operational simplicity of the apparatuses of the present invention and the minimum of safety hazards attendant to the contemplated complete instrument assembly should permit routine use of the instrument assembly by a broad spectrum of laboratory personnel.

Because the apparatuses of the present invention are of simple design and contain no costly materials (with the exception of short lengths of wire made from platinum or other relatively chemically inert metal), they are inexpensive to fabricate. The minimum of moving parts—none in the apparatuses, themselves—and the absence of components required to withstand excessive physical stresses during normal operation of the aforesaid complete instrument assembly should translate into low maintenance and repair costs. Part replacements should be confined primarily to gaskets and membranes; interrogation cells should fail only as a result of careless handling.

Additional objects and advantages of my invention will become evident from the descriptions of the operation of the preferred embodiment which follow when they are considered in conjunction with the accompanying figures and their description. However, it must be appreciated that because the present invention provides new methods and apparatuses for making physical-chemical measurements based on a recently formulated and heretofore unpublished theory, additional advantages of the present invention over the prior art and additional uses to which it is put will not be apparent until the present invention has been for some duration at the disposal of qualified specialists in the various disciplines engaged in the study of macro-ions.

BRIEF DESCRIPTION OF THE FIGURES

FIG. 4a is an exploded perspective of the cell block of the preferred embodiment fitted with one set of components including an interrogation cell; selected elements are not depicted for reasons of clarity. Also depicted are axes along which beams of optical energy are directed.

FIG. 6a is an exploded perspective of a second set of cell-block components including an interrogation cell; selected components are not depicted for reasons of clarity. Also depicted is an axis along which a beam of optical energy is directed.

FIG. 6b is a perspective of the components depicted in FIG. 6a assembled for placement in the cell block. Also depicted are axes along which beams of optical energy are directed.

FIG. 6c is a front, cross-sectional view of the assembled components depicted in FIG. 6b; selected elements are not depicted for reasons of clarity.

FIG. 6d is an elevated view of the lower cell-block assembly fitted with selected components depicted in FIG. 6b. Also depicted are axes along which beams of optical energy are directed.

FIG. 7a is an exploded perspective of a third set of cell-block components including three interrogation cells; selected elements are not depicted for reasons of clarity.

FIG. 7b is a perspective of the components depicted in FIG. 7a assembled for placement in the cell block. Also depicted are axes along which beams of optical energy are directed.

FIG. 7c is a front, cross-sectional view of the assembled components depicted in FIG. 7b; selected elements are not depicted for reasons of clarity.

FIG. 9a is a rear-facing, sectional view of the lower instrument assembly through line 9a—9a depicted in FIG. 8b exposing the inner face of the front wall; the cell block is removed.

FIG. 9b is a fragmentary, front, sectional view of the lower instrument assembly through line 9b—9b depicted in FIG. 8b exposing a portion of the inner face of the rear wall; the cell block is removed.

FIG. 10 is an elevated, schematic view of a design for a steady-state electrophoresis instrument assembly accommodating one preferred embodiment of the present invention and featuring among its principal components a Rayleigh interference optical system; selected elements of the instrument assembly are omitted for reasons of clarity. Also depicted are axes along which the beams of optical energy of the Rayleigh optical system are directed.

FIG. 11a is a fragmentary, front, cross-sectional view of the preferred embodiment fitted with the interrogation cell depicted in FIGS. 3a and 4a. The preferred embodiment is charged with solvent and the interrogation cell is charged with a macro-ion sample (prior to the application of a directed electrical field).

FIG. 11b depicts the view seen in FIG. 11a after the macro-ions have achieved electrophoretic steady state.

FIG. 12a is a schematic representation of a typical optical record produced by a Rayleigh interference optical system interrogating the preferred embodiment which is fitted with the interrogation cell depicted in FIGS. 11a and 11b; the interrogation cell is charged only with solvent.

FIG. 12b is another schematic representation of a typical optical record produced by a Rayleigh interference optical system interrogating the preferred embodiment which is fitted with the interrogation cell depicted in FIGS. 11a and 11b; the interrogation cell is charged with solvent and a macro-ion sample. A directed electrical field is present and the macro-ion sample has achieved electrophoretic steady state.

DESCRIPTION OF THE PREFERRED EMBODIMENT

Figure 1A:
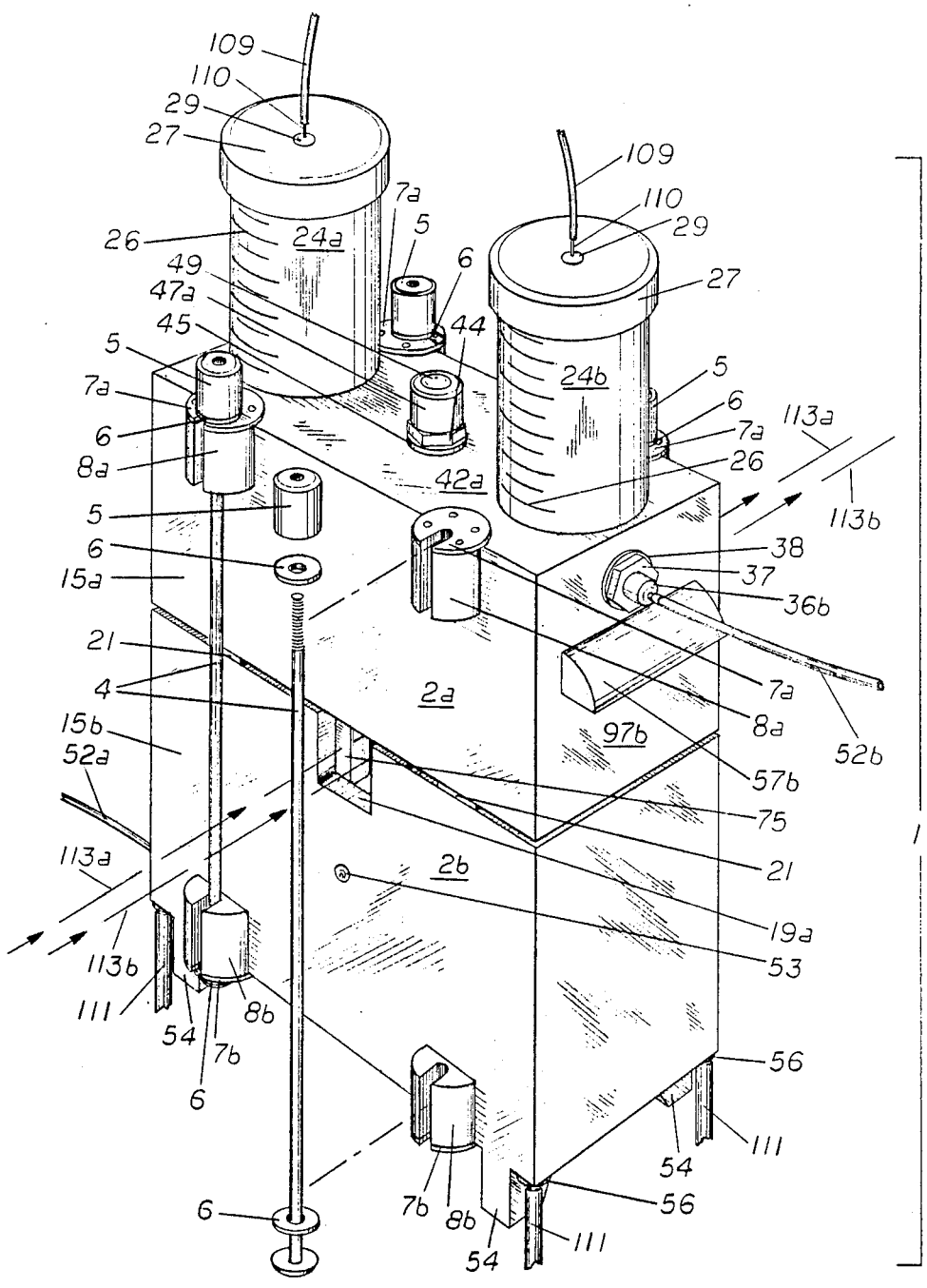
FIG. 1a is a perspective of the preferred embodiment of the present invention with selected elements depicted in partially exploded view; also depicted are axes along which beams of optical energy are directed.
Figure 1B:
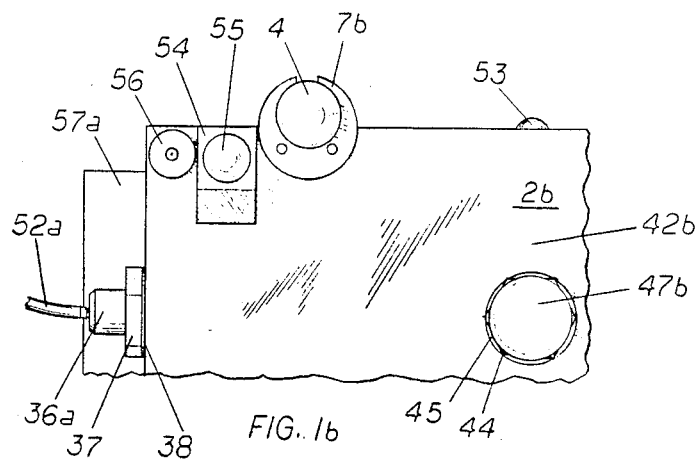
FIG. 1b is a fragmentary, underside view of the preferred embodiment.
Figure 4B:
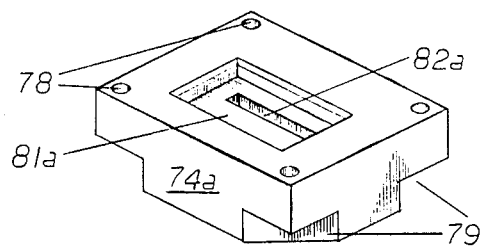
FIG. 4b is a perspective of the upper cell-block assembly, inverted to depict its underside.
Figure 4C:
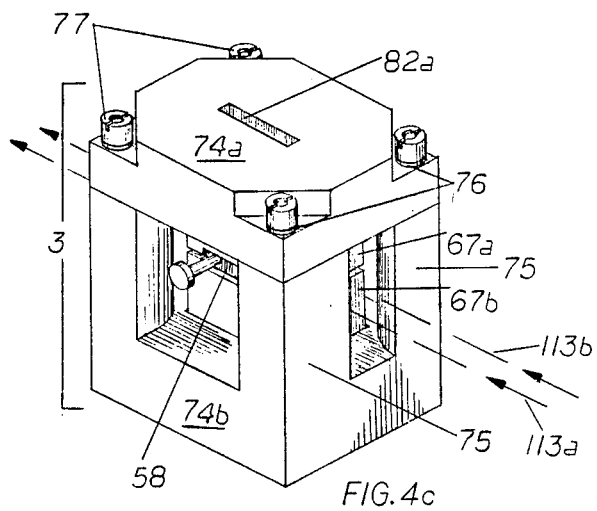
FIG. 4c is a perspective of the cell block fitted with the components depicted in FIG. 4a. Also depicted are axes along which beams of optical energy are directed.
Figure 5A:
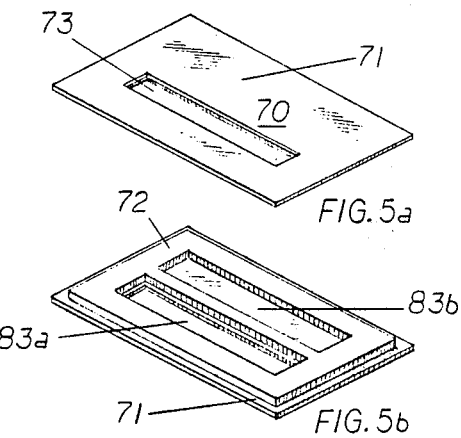
FIG. 5a is a perspective of the compound gasket of the cell block.
Figure 5B:
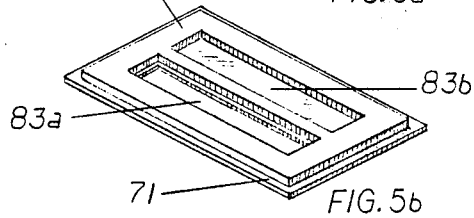
FIG. 5b is another perspective of the compound gasket.

The preferred embodiment 1 of the present invention (FIG. 1a), hereafter in this section of the present disclosure also referred to as the instrument 1, is comprised of three principal assemblies: an upper instrument assembly 2a, a lower instrument assembly 2b, and a cell block 3 (FIG. 4c) fitted with its constituent compound gaskets 70 and one of several cell-block-component embodiments 99, 100, and 101 (FIGS. 4a, 6b, and 7b).

Figure 8A:
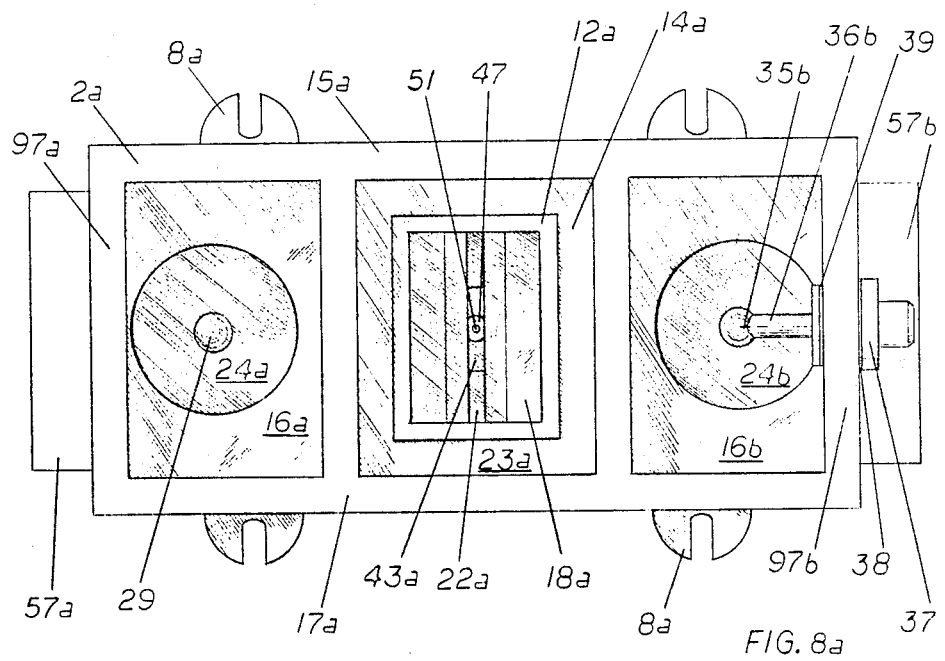
FIG. 8a is an underside view of the upper instrument assembly.
Figure 8B:
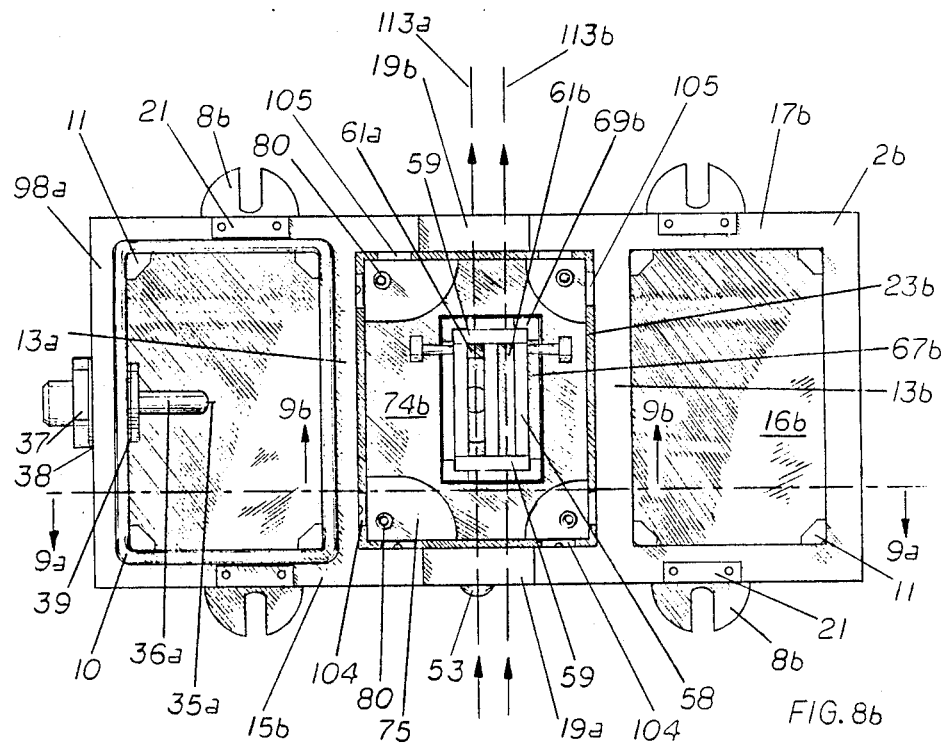
FIG. 8b is an elevate view of the lower instrument assembly fitted with the lower cell-block assembly and selected components depicted in FIGS. 3a and 4a; also depicted are axes along which beams of optical energy are directed.

With particular reference to FIGS. 1a through 3b, the upper and lower instrument assemblies 2a and 2b are fabricated, except as specifically noted otherwise in this disclosure, from a transparent, nonelectrically conducting material (e.g., polymethylmethacrylate cast sheet). The instrument 1 is assembled by first seating the cell block 3 containing its constituent elements into the lower cell-block compartment 23b of the lower instrument assembly 2b (FIG. 9a; see below), and then fitting the upper instrument assembly 2a to the lower instrument assembly 2b. Eight guide posts 11, fabricated from a nonelectrically conducting material (e.g., nylon) and bonded to the lower instrument assembly 2b (FIGS. 8b and 9a), project into the upper instrument assembly 2a to effect a snug, substantially reproducible fit between the upper and lower instrument assemblies 2a and 2b. The upper and lower instrument assemblies 2a and 2b are held firmly together by four metallic bolts 4 (e.g., of stainless steel); each bolt 4 is fitted with a metallic nut 5 (e.g., of stainless steel) and two nonmetallic washers 6 (e.g., of nylon). The washers 6 seat against upper and lower slotted contact plates 7a and 7b (e.g., of stainless steel) fastened respectively to the top and bottom walls 42a and 42b of the instrument 1 and also respectively to upper and lower slotted flanges 8a and 8b. The nuts 5 screw down until the upper instrument assembly 2a contacts the four stop plates 21 (e.g., of Teflon) attached to the front and rear walls 15b and 17b of the lower instrument assembly 2b (FIGS. 8b and 9a). Other suitable fasteners may also be used to couple the upper and lower instrument assemblies 2a and 2b together.

Four identical legs 54 fitted with four identical feet 55 (e.g., of hard rubber) are located on the bottom wall 42b of the instrument 1. For procedures leading to its operation, except as specifically noted otherwise in this disclosure, the assembled instrument 1 is supported by the legs 54 on an substantially horizontal surface. During operation, the instrument 1 is also maintained in this spatial orientation supported by four mount pins 111, elements of a precision optical mount (not shown; see below), which engage four metallic (e.g., stainless steel), dimpled mount studs 56 anchored in the bottom wall 42b of the instrument 1. This normative spatial orientation of the preferred embodiment 1 constitutes the physical frame of reference for the FIGURES and descriptions of this disclosure pertaining to the preferred embodiment 1 and its several subassemblies, as represented by cell-block-component embodiments 99, 100, and 101.

When the instrument I is assembled, two O-rings 10 (e.g., of neoprene) held in place by the eight guide posts 11 effect a fluid-tight seal between the upper and lower instrument assemblies 2a and 2b. Similarly, when the instrument 1 is assembled, the upper cell-block gasket 12a (e.g., of neoprene) which is bonded to the upper cell-block-support railing 14a effects a fluid-tight seal between the cell block 3 and the upper instrument assembly 2a; and the lower cell-block gasket 12b (e.g., of hard rubber) which is bonded to the lower cell-block-support railing 14b effects a fluid-tight seal between the cell block 3 and the lower instrument assembly 2b. Two solvent chambers 133a and 133b are located within the instrument 1. An upper partition 18a divides the solvent chamber 133a into an outer chamber 16a and an upper inner chamber 20a; similarly, a lower partition 18b divides the solvent chamber 133b into an outer chamber 16b and a lower inner chamber 20b. An upper partition slot 22a, extending from the front wall 15a to the rear wall 17a of the upper instrument assembly 2a, provides a restricted area passage between the upper inner chamber 20a and the outer chamber 16a. A lower partition slot 22b, extending from the front wall 15b to the rear wall 17b of the lower instrument assembly 2b, similarly provides a restricted area passage between the lower inner chamber 20b and the outer chamber 16b.

Bonded to the top wall 42a and open to the outer chambers 16a and 16b are respective identical tubular gas towers 24a and 24b. Bonded to the gas towers 24a and 24b are respective exteriorly-threaded collars 25a and 25b which accept removable, interiorly-threaded, gas-tower caps 27. Gas-tight seals between the gas-tower caps 27 and the gas towers 24a and 24b are effected by gaskets 28 (e.g., of hard rubber) when the gas-tower caps 27 are secured to the gas towers 24a and 24b. The collars 25a and 25b and gas-tower caps 27 are fabricated from a nonelectrically conducting material (e.g., nylon). The gas towers 24a and 24b possess identical sets of horizontal, uniformly spaced gas-tower calibration lines 26 scribed at 0.5 cm, or other convenient, intervals. A self-sealing valve 29 (e.g., of neoprene; see below) extends through the center of each gas-tower cap 27.

An extension tube 30 having the same transverse cross-sectional dimensions as the gas towers 24a and 24b can be attached to either gas tower, as represented by gas tower 24a, by means of an interiorly-threaded collar 31, bonded to the extension tube 30, which accepts the collars 25a and 25b. A fluid-tight seal between either gas-tower, as represented by gas tower 24a, and the extension tube 30 is effected by a gasket 32 (e.g., of hard rubber) when the extension tube 30 is attached to either gas tower, as represented by gas tower 24a. An exteriorly-threaded collar 33 which is bonded to the extension tube 30 and is identical to the collars 25a and 25b, accepts a gas-tower cap 27. The collars 31 and 33 are fabricated from the same material as the collars 25a and 25b. The extension tube 30 possesses a set of horizontal, uniformly spaced, extension-tube calibration lines 34 scribed at 0.5 cm, or other convenient, intervals which is similar to the sets of gas-tower calibration lines 26.

The outer chambers 16a and 16b are each fitted with respective identical electrodes 35a and 35b fabricated from platinum or other relatively chemically inert metal wire. The electrodes 35a and 35b are sealed within identical exteriorly-threaded electrode fittings 36a and 36b, respectively, which are fabricated from a nonelectrically conducting material (e.g., nylon). The electrode fittings 36a and 36b extend through the respective outer, lateral walls 98a and 97b of the lower and upper instrument assemblies 2b and 2a, respectively, and are secured by nuts 37 and washers 38; the nuts 37 and washers 38 are fabricated from a nonelectrically conducting material (e.g., nylon). Gaskets 39 (e.g., of hard rubber) ensure fluid-tight seals between the electrode fittings 36a and 36b and the respective outer lateral walls 98a and 97b. Conventional female electrical jacks 40a and 40b which make firm electrical contact, respectively, with the electrodes 35a and 35b are bonded in respective electrode fittings 36a and 36b.

Identical exteriorly-threaded upper and lower sample-loading-port fittings 43a and 43b which are secured by nuts 44 and washers 45 extend, respectively, through the top and bottom walls 42a and 42b of the instrument 1. The upper and lower sample-loading-port fittings 43a and 43b are centered, respectively, above the upper partition slot 22a and below the lower partition slot 22b. The upper and lower sample-loading-port fittings 43a and 43b, nuts 44, and washers 45 are fabricated from a nonelectrically conducting material (e.g., nylon). Gaskets 46 (e.g., of hard rubber) effect fluid-tight seals between the upper and lower sample-loading-port fittings 43a and 43b and the top and bottom walls 42a and 42b of the instrument 1, respectively. Upper and lower sample-loading ports 41a and 41b extend, respectively, through the upper and lower sample-loading port fittings 43a and 43b. The upper sample-loading-port fitting 43a is engaged by an interiorly-threaded, hollow-stemmed, upper sample-loading-port stopper 47a fabricated from a nonelectrically conducting material (e.g., nylon). A self-sealing valve 49 (e.g., of neoprene) is bonded in the top of the upper sample-loading-port topper 47a with the valve channel 50 aligned with the stopper channel 51 located in the upper sample-loading-port stopper 47a. All self-sealing valves, as represented by self-sealing valve 49, fitted to the preferred embodiment 1 are similar in function and design to self-sealing valves often fitted to inflatable game balls (e.g., basketballs of selected design). The self-sealing valves of the instrument 1, as represented by self-sealing valve 49, can accept a hollow-stemmed needle, such as a syringe needle, which makes a fluid- and/or gas-tight seal in the valve channel, as exemplified by valve channel 50, allowing fluid or gas to be introduced into or out of the instrument 1 through the said hollow-stemmed needle. When the hollow-stemmed needle is withdrawn, the valve channel, as represented by valve channel 50, closes automatically to form a fluid-and/or gas-tight seal.

A lower sample-loading-port stopper 47b engages the lower sample-loading-port fitting 43b. The lower sample-loading-port stopper 47b is similar to the upper sample-loading-port stopper 47a except that the lower sample-loading-port stopper 47b is solid throughout and lacks a self-sealing valve, as represented by self-sealing valve 49. When the upper and lower sample-loading-port stoppers 47a and 47b are seated in the respective upper and lower sample-loading-port fittings 43a and 43b, fluid-tight seals are effected by gaskets 48 (e.g., of hard rubber) between the upper and lower sample-loading-port stoppers 47a and 47b and the respective upper and lower sample-loading-port fittings 43a and 43b.

Figure 3A:
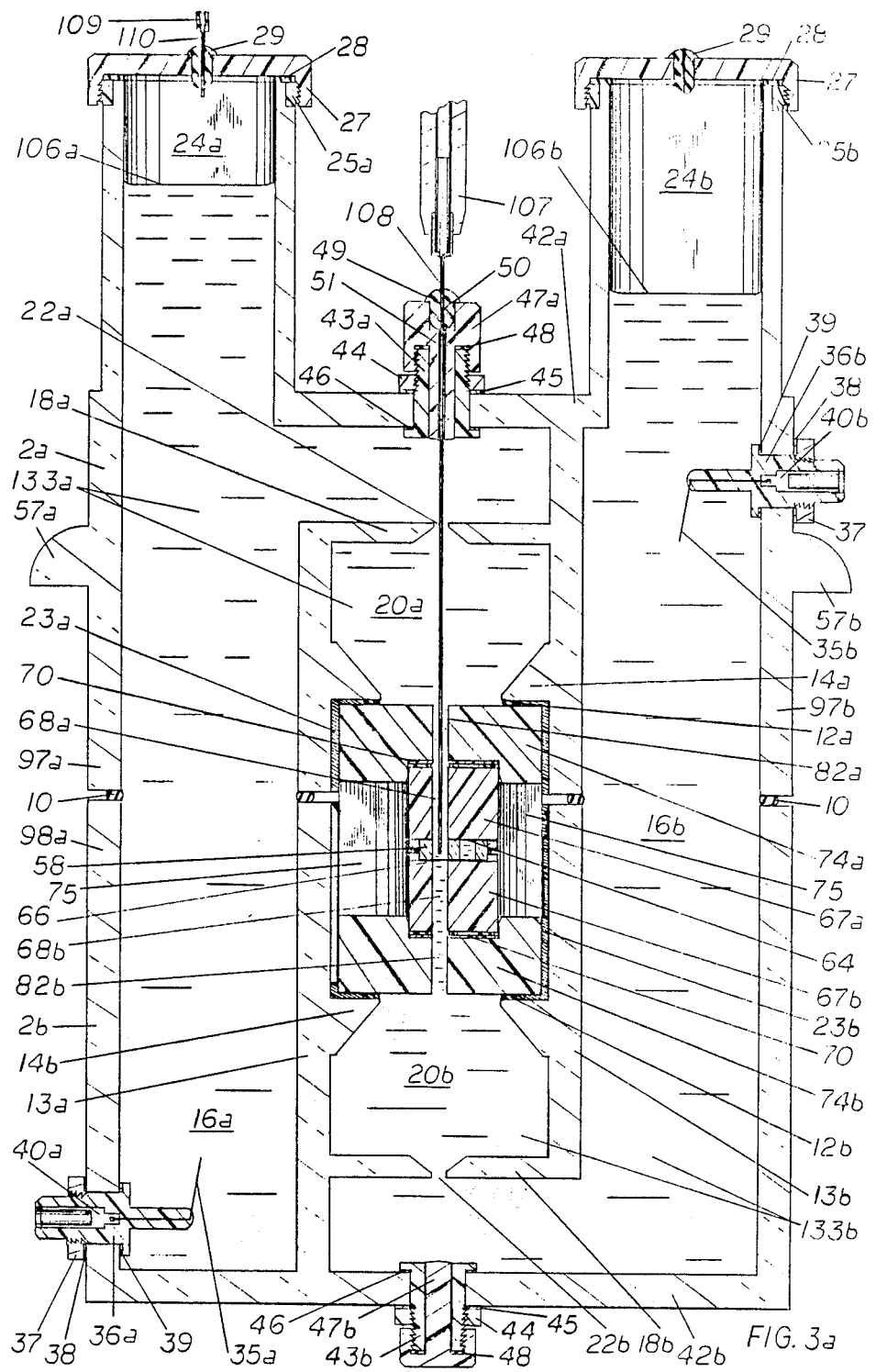
FIG. 3a is a front, cross-sectional view of the preferred embodiment through its midline; the preferred embodiment is charged with solvent. Also depicted in fragmentary view is a syringe in position for charging the preferred embodiment with a macro-ion sample. Selected elements located on the bottom wall of the preferred embodiment are not depicted for reasons of clarity.
Figure 3B:
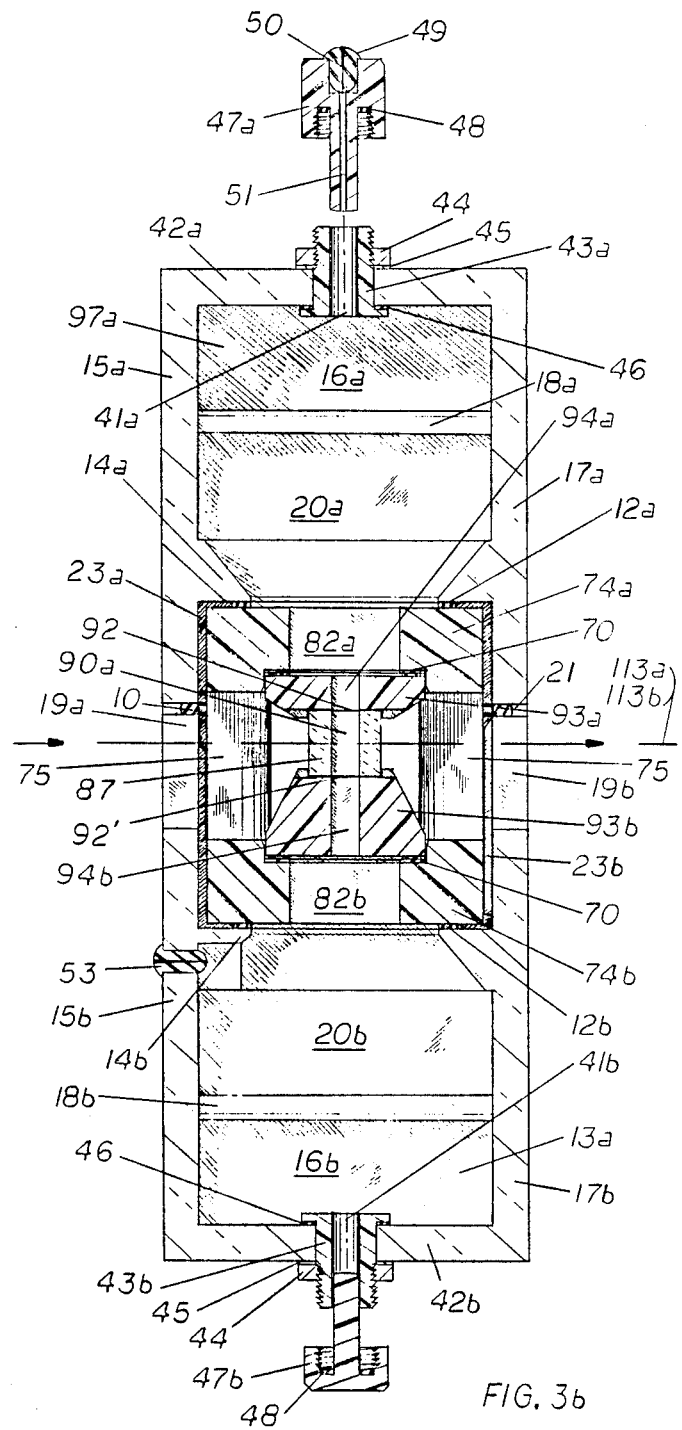
FIG. 3b is a lateral, cross-sectional view of the preferred embodiment through its midline with some components shown in partially exploded view; selected elements are not depicted for reasons of clarity. Also depicted are axes along which beams of optical energy are directed.

An additional self-sealing valve 53 (e.g., of neoprene) extends through the front wall 15b of the lower instrument assembly 2b; the design of the lower cell-block-support railing 14b is modified to allow the self-sealing valve 53 access to the lower inner chamber 20b (FIGS. 3b and 9a). Projections 57a and 57b located on respective outer lateral walls 97a and 97b of the upper instrument assembly 2a function as handles for the instrument 1.

With particular reference to FIGS. 3a and 4a through 5b, a rectangular interrogation cell 58 features two cell walls 134a and 134b and a cell partition 60; the cell partition 60 divides the interrogation cell 58 into two identical, rectangular interrogation chambers 61a and 61b. The interrogation chambers 61a and 61b are further bounded by two identical, parallel, planar optical energy transmitting windows 59 which define optical energy entry and exit ports for interrogating beams of optical energy aligned along substantially parallel axes 113a and 113b, as explained below. All interrogation cells referred to in this disclosure, as represented by interrogation cell 58, are fabricated from fused, optical silica exhibiting high transmission throughout the visible spectrum and preferably a large portion of the ultraviolet spectrum as well. The interrogation chambers 61a and 61b are not enclosed at the top or bottom by elements of the interrogation cell 58. The interrogation chambers 61a and 61b are served by respective cell-filling ports 62a and 62b. The two cell-filling ports 62a and 62b are concentric and are fitted with identical, removable cell-filling-port stoppers 63 (e.g., of Teflon) which, when seated in the cell-filling ports 62a and 62b, make fluid-tight seals with, and completely fill, the cell-filling ports 62a and 62b; however, the cell-filling-port stoppers 63 do not project into the interrogation chambers 61a and 61b when seated in the cell-filling ports 62a and 62b.

The interrogation cell 58 is intercalated between a cell gasket 64, above, and a semipermeable membrane 66, below; both the cell gasket 64 and semipermeable membrane 66 possess exterior dimensions in the horizontal plane identical, to the corresponding exterior dimensions of the interrogation cell 58. All semipermeable membranes described in this disclosure as represented by semipermeable membrane 66 are fabricated from one of several commercially available semipermeable membranous materials which are employed in biological and other research (for example, to concentrate solutions of macromolecules by the technique of reverse osmosis). The said membranous materials have in common the property of being permeable to small molecules and ions (e.g., $Cl^-$) but impermeable to larger molecules (e.g., proteins). The said membranous materials are sometimes comprised of a porous lattice of cellulose fibers (e.g., Spectra/Por 1 from Spectrum Medical Industries Inc., Los Angeles, CA); these cellulosic films are often characterized by the molecular weight of the smallest globular protein which they retain under a standard set of test conditions. The cell gasket 64 is fabricated from the same material as the semipermeable membrane 66 or from other membranous materials of approximately the same thickness as the semipermeable membrane 66 and possessing fluid-sealing properties (e.g., polyethylene).

The cell gasket 64, interrogation cell 58, and semipermeable membrane 66 are intercalated between an upper cell-support piece 67a and a lower cell-support piece 67b. All cell-support pieces, as represented by upper cell-support piece 67a, referred to in this disclosure are fabricated from a nonelectrically conducting material (e.g., Kydex from Rohm and Haas, Philadelphia, PA). The upper and lower cell-support pieces 67a and 67b feature identical respective discontinuous rims 69a and 69b which align the interrogation cell 58, cell gasket 64, semipermeable membrane 66, and upper and lower cell-support pieces 67a and 67b in a substantially reproducible manner.

The interrogation cell 58, cell gasket 64, semipermeable membrane 66, and upper and lower cell-support pieces 67a and 67b constitute one of several cell-block-component embodiments described in this disclosure and is designated by reference character 99. When assembled, all cell-block-component embodiments, as represented by cell-block-component embodiment 99, are identical in height, and when secured in the cell lock 3, each embodiment, as represented by cell-block-component embodiment 99, is held in a substantially reproducible alignment under mild compression between two identical compound gaskets 70.

The compound gaskets 70 are each comprised of a soft-rubber component 72 (e.g., of neoprene) and a thinner component 71 (e.g., of polyethylene or hard rubber) which are bonded together. The thinner component 71 is dimenionally rigid in the horizontal plane and also possesses fluid sealing properties. When assembled within the cell block 3, the soft-rubber components 72 contact the cell-support pieces of the cell-block-component embodiments, as represented by upper cell-support piece 67a of cell-block-component embodiment 99. The dimensions of the thinner component 71 in the horizontal plane are the same as the corresponding exterior dimensions of the upper and lower cell-support pieces 67a and 67b. The edges of the thinner component 71 extend an equal distance (approximately −1 mm) on all four sides beyond the corresponding edges of the thicker, soft-rubber component 72.

The soft-rubber component 72 of each compound gasket 70 features two identical, symmetrically disposed, rectangular cutouts 83a and 83b. The cutout 83a is aligned coextensively with a smaller rectangular hole 73 of the thinner component 71; consequently, the four sides of the cutout 83a are disposed an equal distance (approximately 0.3 mm) away from the corresponding four edges of the rectangular hole 73.

The compound gaskets 70 and the upper and lower cell-support pieces of the cell-block-component embodiments, as represented by upper and lower cell-support pieces 67a and 67b of cell-block-component embodiment 99, seat snugly and in a substantially reproducible manner into respective upper and lower cell-block wells 81a and 81b located in upper and lower cell-block assemblies 74a and 74b, respectively; when assembled, the upper and lower cell-block assemblies 74a and 74b constitute the cell block 3. The upper and lower cell-block wells 81a and 81b ensure a substantially reproducible alignment between each cell-block-component embodiment, as represented by cell-block-component embodiment 99, the two compound gaskets 70, and the upper and lower cell-block assemblies 74a and 74b when each cell-block-component embodiment, as represented by cell-block-component embodiment 99, and the compound gaskets 70 are secured in the cell block 3. The upper and lower cell-block assemblies 74a and 74b are fabricated from a nonelectrically conducting material (e.g., Kydex).

When the cell block 3 is assembled, four threaded, metallic studs 80 (e.g., of stainless steel), one each of which is anchored in each of four upright members 75 of the lower cell-block assembly 74b, engage four stud holes 78 located in the upper cell-block assembly 74a. Each stud 80 fits snugly into its respective stud hole 78 to ensure a substantially reproducible alignment between the upper and lower cell-block assemblies 74a and 74b. The upper and lower cell-block assemblies 74a and 74b are secured firmly together by washers 76 and slotted nuts 77 which fit to the studs 80 and seat in cutouts 79 of the upper cell-block assembly 74a. The slotted nuts 77 are fabricated from the same material as the studs 80; the washers 76 are fabricated from a nonmetallic material (e.g., nylon).

Rectangular holes 68a and 68b located, respectively, in the upper and lower cell-support pieces 67a and 67b; the rectangular hole 65 located in the cell gasket 64; and the interrogation chamber 61a of the interrogation cell 58 possess identical corresponding dimensions in the horizontal plane and are aligned coextensively when the cell-block-component embodiment 99 and the compound gaskets 70 are secured in the cell block 3. The holes 68a, 68b, and 65 and the interrogation chamber 61a form a linear, vertically disposed, rectangular hole with constant cross-sectional dimensions which is interrupted by, and is perpendicular to, the horizontal surfaces of the semipermeable membrane 66. When the cell-block-component embodiment 99 is secured in the cell block 3, the rectangular holes 68a, 68b, and 65 and the interrogation chamber 61a also align coextensively with the rectangular holes 73 of the thinner components 71 of the compound gaskets 70, the rectangular cutouts 83a of the soft-rubber components 72 70, and the rectangular holes 82a and 82b located, respectively, in the upper and lower cell-block assemblies 74a and 74b. The dimensions in the horizontal plane of the rectangular holes 82, 82b, and 73 are identical to the corresponding dimensions of the rectangular holes 68a, 68b, and 65 and the interrogation chamber 61a.

The soft-rubber components 72 of the compound gaskets 70 undergo mild deformation when the cell block 3 is fitted with a cell-block-component embodiment, as represented by cell-block-component embodiment 99, and secured as described. This deformation of the soft-rubber components 72 generates sufficient pressure within the cell block 3 to create fluid-tight seals between adjacent members of the train of components within the cell block 3. The presence of the rectangular cutout 83b ensures that, when a cell-block-component embodiment, as represented by cell-block-component embodiment 99, and the two compound gaskets 70 are assembled in the cell block 3, the forces exerted by the deformed soft-rubber components 72 are applied substantially evenly over the surfaces of the juxtaposed upper and lower cell-support pieces, as represented by upper and lower cell-support pieces 67a and 67b.

With particular reference to FIGS. 3b, and 6a through 6d, cell-block-component embodiment 100 features a rectangular interrogation cell 87 intercalated between identical upper and lower semipermeable membranes 92 and 92'. The interrogation cell 87 features a single interrogation chamber 90 bounded by cell walls 135a and 135b and two identical, parallel, planar optical energy transmitting windows 88 which define optical energy entry and exit ports for an interrogating beam of optical energy aligned along the axis 113a, as explained below. The interrogation chamber 90 is open at the top and bottom and has the same lateral dimension as the interrogation chambers 61a and 61b of the interrogation cell 58. The interrogation chamber 90 is served by a cell-filling port 91 which receives a cell-filling-port stopper 63; the cell-filling-port stopper 63 makes a fluid-tight seal and completely fills the cell-filling port 91 but does not project into the interrogation chamber 90 when seated in the cell-filling port 91.

The interrogation cell 87 is taller and has a shorter optical path than the interrogation cell 58. The dimensions of the upper and lower semipermeable membranes 92 and 92' in the horizontal plane are identical to the corresponding exterior dimensions of the interrogation cell 87. The interrogation cell 87 and the upper and lower semipermeable membranes 92 and 92' are intercalated between upper and lower cell-support pieces 93a and 93b. Identical discontinuous rims 95a and 95b of the respective upper and lower cell-support pieces 93a and 93b align the upper and lower cell-support pieces 93a and 93b, the interrogation cell 87, and the upper and lower semipermeable membranes 92 and 92' in a substantially reproducible manner. The lower cell-support piece 93b also features a support post 89 capped by a support-post pad 131 (e.g., of neoprene) which makes firm contact with the upper cell-support piece 93a when the cell-block-component embodiment 100 is secured in the cell block 3. The support post 89 and the interrogation cell 87 define the sides of an open reference-beam channel 132 for a beam of optical energy aligned along the axis 113b, as explained below. The dimensions of the upper and lower cell-support pieces 93a and 93b in the horizontal plane where the upper and lower cell-support pieces 93a and 93b contact the compound gaskets 70 are identical to the corresponding dimensions of the thinner component 71 in order that the upper and lower cell-support pieces 93a and 93b fit snugly and in a substantially reproducible manner into the respective upper and lower cell-block wells 81a and 81b.

The rectangular holes 94a and 94b located in the respective upper and lower cell-support pieces 93a and 93b and the interrogation chamber 90 of the interrogation cell 87 possess identical corresponding dimensions in the horizontal plane and align coextensively when the cell-block-component embodiment 100 and the two compound gaskets 70 are secured in the cell block 3. The holes 94a and 94b, and the interrogation chamber 90 form a linear, vertically disposed, rectangular hole with constant cross-sectional dimensions which is interrupted by, and is perpendicular to, the horizontal surfaces of the upper and lower semipermeable membranes 92 and 92'. When the cell-block-component embodiment 100 is secured in the cell block 3, the rectangular holes 94a and 94b and the interrogation chamber 90 are also aligned coextensively with the rectangular holes 73 of the thinner components 71 of the compound gaskets 70, the rectangular cutouts 83a of the soft-rubber components 72, and the rectangular holes 82a and 82b located, respectively, in the upper and lower cell-block assemblies 74a and 74b. However, the holes 94a and 94b and the interrogation chamber 90 are shorter than the holes 73, 82a, and 82b and the cutouts 83a in the horizontal dimension normal to the cell windows 88 (FIG. 3b); the result is a pronounced stair-step configuration where the rectangular holes 94a and 94b of the respective upper and lower cell-support pieces 93a and 93b contact the larger cutouts 83a of the soft-rubber components 72.

With particular reference to FIGS. 7a, 7b, and 7c, the cell-block-component embodiment 101 features an upper interrogation cell 58', a middle interrogation cell 58'', and a lower interrogation cell 58''', intercalated among four semipermeable membranes 66. The semipermeable membranes 66 of the cell-block-component embodiment 101 are identical to the semipermeable membrane 66 of the cell-block-component embodiment 99; and the interrogation cells 58', 58'', and 58''' are identical to the interrogation cell 58 of the cell-block-component embodiment 99 and feature identical, respective planar optical energy transmitting windows 59', 59'', and 59'' which define optical energy entry and exit ports for interrogating beams of optical energy aligned along the axes 113a and 113b, as explained below. The interrogation cells 58', 58'', and 58''', and the semipermeable membranes 66 are held between an upper cell-support piece 84a and a lower cell-support piece 84b. The upper and lower cell-support pieces 84a and 84b have the same design and dimensions as the upper and lower cell-support pieces 67a and 67b, respectively, of the cell-block-component embodiment 99 except that the upper and lower cell-support pieces 84a and 84b feature respective identical discontinuous rims 86a and 86b which are taller than the discontinuous rims 69a and 69b of respective upper and lower cell-support pieces 67a and 67b; and the upper cell-support piece 84a is shorter (vertical dimension) than the upper cell-support piece 67a. The discontinuous rims 86a and 86b align the interrogation cells 58', 58", and 58"', the semipermeable membranes 66, and the upper and lower cell-support pieces 84a and 84b in a substantially reproducible manner. The middle interrogation cell 58" is reversed in its orientation with respect to the upper and lower interrogation cells 58' and 58"' to allow adequate space for the cell-filling-port stoppers 63 when the stoppers 63 are fitted in the cell-filling ports 62a' and 62b' of the upper interrogation cell 58', the cell-filling ports 62a" and 62b" of the middle interrogation cell 58", and the cell-filling ports 62a"' and 62b"' of the lower interrogation cell 58"'.

Rectangular holes 85a and 85b located, respectively, in the upper and lower cell-support pieces 84a and 84b, and the interrogation chambers 61a', 61b", and 61a"' of the interrogation cells 58', 58", and 58"', respectively, possess identical corresponding dimensions in the horizontal plane and are aligned coextensively when the cell-block-component embodiment 101 and the two compound gaskets 70 are secured in the cell block 3. The holes 85a and 85b and the interrogation chambers 61a', 61b", and 61a"' form a linear, vertically disposed, rectangular hole with constant cross-sectional dimensions which is interrupted by, and is perpendicular to, the horizontal surfaces of the semipermeable membranes 66. When the cell-block-component embodiment 101 is secured in the cell block 3, the rectangular holes 85a and 85b and the interrogation chambers 61a', 61b", and 61a"' also align coextensively with the rectangular holes 73 of the thinner components 71 of the compound gaskets 70, the rectangular cutouts 83a of the soft-rubber components 72, and the rectangular holes 82a and 82b located respectively in the upper and lower cell-block assemblies 74a and 74b. The dimensions in the horizontal plane of the rectangular holes 82a, 82b, and 73 are identical to the corresponding dimensions of the rectangular holes 85a and 85b and the interrogation chambers 61a', 61b", and 61a"'.

It will be readily apparent to those skilled in the general area of the art encompassing the present invention that, by appropriate modifications of the upper and lower cell-support pieces, as represented by upper and lower cell-support pieces 67a and 67b, and the membranous elements, as represented by semipermeable membrane 66 and cell gasket 64, interrogation cells of many different dimensions in addition to the interrogation cells, as represented by interrogation cell 58, described above and depicted in the FIGURES can be accommodated effectively, either singly or multiply in series, within the cell block 3. Accordingly, cell-block-component embodiments 99, 100, and 101 are representative only of the many cell-block-component embodiments of differing design, as exemplified by cell-block-component embodiment 99, which could be fitted to the cell block 3.

With particular reference to FIGS. 8b, 9a, and 9b, four identical, metallic (e.g., stainless steel), flat springs 104 are located in the lower cell-block compartment 23b of the lower instrument assembly 2b; two flat springs 104 are secured to the front wall 15b of the lower instrument assembly 2b, and two flat springs 104 are secured to the left lateral wall 13a of the lower cell-block compartment 23b. When the cell block 3 is inserted into the lower cell-block compartment 23b, the flat springs 104 press the cell block 3 tightly against four nonmetallic (e.g., nylon) aligning stops 105; two aligning stops 105 are bonded to the rear wall 17b of the lower instrument assembly 2b, and two aligning stops 105 are bonded to the right lateral wall 13b of the lower cell-block compartment 23b. This configuration of the flat springs 104 and the aligning stops 105 ensures that the front-to-rear and lateral alignments of the cell block 3 in the lower cell-block compartment 23b are substantially reproducible. The upper cell-block compartment 23a located in the upper instrument assembly 2a contain neither flat springs nor aligning stops, as represented by flat springs 104 and aligning stops 105.

With the upper instrument assembly 2a secured in place upon the lower instrument assembly 2b, pressure exerted by the soft, upper cell-block gasket 12a presses the cell block 3 against the harder, lower cell-block gasket 12b to effect a substantially reproducible vertical alignment of the cell block 3 in the instrument 1, in addition to fluid-tight seals between the cell block 3 and the upper and lower cell-block gaskets 12a and 12b. Rectangular cutouts 19a and 19b in the front wall 15b and rear wall 17b, respectively, of the lower instrument assembly 2b allow the interrogation cell(s), as represented by the interrogation cell 58, fitted in the cell block 3 to be interrogated by an optical system (see below), as exemplified by Rayleigh interference optical system 115 (FIG. 10).

Before the instrument 1 is prepared for one or more electrophoretic steady-state analyses, a choice is made of the type and number of interrogation cells, as represented by interrogation cell 58, to be fitted to the cell block 3. Longer optical-path interrogation cells, as exemplified by interrogation cell 58, are preferred for analyses in which data at low macro-ion concentrations are of particular interest; shorter optical-path interrogation cells, as exemplified by interrogation cell 87, are useful in analyses requiring electrophoretic steady-state data at higher macro-ion concentrations. For the majority of analyses, shorter (vertical dimension) interrogation cells, as represented by interrogation cell 58, are of adequate dimensions to contain the macro-ion concentration gradients formed at electrophoretic steady state; however, analyses of selected macro-ion systems require taller interrogation cells, as represented by interrogation cell 87 (see below). Multi-cell operation, as represented by the employment of the cell-block-component embodiment 101 in the instrument 1, allows several electrophoretic steady-state analyses to be conducted simultaneously; on the other hand, single-cell operation with one semipermeable membrane, as represented by the employment in the instrument 1 of the cell-block-component embodiment 99 fitted with one semipermeable membrane 66, allows rapid turnaround between analyses (see below).

The choice of whether single-chamber interrogation cells, as represented by interrogation cell 87, or double-chamber interrogation cells, as represented by interrogation cell 58, are fitted to the instrument 1 is determined by the technical requirements of the optical system employed to interrogate the macro-ions to be analyzed at electrophoretic steady state. Single-chamber interrogation cells as exemplified by interrogation cell 87 fitted to the instrument 1 are appropriately interrogated by single-beam absorption optical systems or by a Rayleigh interference optical system fitted with an adjustable optical-path compensator, as exemplified by adjustable optical-path compensator 130 of Rayleigh interference optical system 115 (FIG. 10; see below). Double-chamber interrogation cells as exemplified by interrogation cell 58 fitted to the instrument 1 are appropriately interrogated by dual-beam optical systems; however, an adjustable optical-path compensator as exemplified by adjustable optical-path compensator 130 is not a required element in a Rayleigh interference optical system employed to interrogate macro-ions at electrophoretic steady state in double-chamber interrogation cells, as represented by interrogation cell 58, fitted to the instrument 1.

The components of each cell-block-component embodiment, as represented by cell-block-component embodiment 99 (FIG. 4), are assembled in the order illustrated and described earlier. In single-cell operation, the upper membranous element may be either a second semipermeable membrane (see below), as exemplified by semipermeable membrane 66, or a cell gasket, as exemplified by cell gasket 64 shown in FIG. 4a. In multi-cell operation, semipermeable membranes, as represented by semipermeable membrane 66, are disposed above and below all interrogation cells present, as represented by upper, middle, and lower interrogation cells 58', 58", and 58''' of cell-block-component embodiment 101. Following assemblage( the cell-block-component embodiment, as exemplified by cell-block-component embodiment 99, and the two compound gaskets 70 are secured in the cell block 3, as described earlier.

If one or more double-chamber interrogation cells as exemplified by interrogation cell 58 of cell-block-component component embodiment 99 are fitted to the instrument 1, one interrogation chamber, designated the reference interrogation chamber, of each interrogation cell present in the cell block 3, as represented by interrogation chamber 61b of interrogation cell 58, is charged with solvent before the cell block 3 is fitted to the lower instrument assembly 2b. The reference interrogation chambers of the interrogation cells fitted in cell block 3, as exemplified by interrogation chamber 61b of interrogation cell 58, are aligned coextensively with the cutouts 83b of the soft-rubber components 72 of the two compound gaskets 70 fitted to the cell block 3. Typically, the solvent is a dilute, pH-buffered, aqueous solution of an inorganic salt (e.g., KCl). Higher salt concentrations are sometimes used and solvents may also contain organic salts as well; in some instances, nonaqueous polar solvents are used.

The solvent-charging procedure is very similar for the cell-block-component embodiments 99 and 101 and is illustrated below by the procedure followed with the cell-block-component embodiment 99: With the cell block 3 oriented to allow air to escape from the cell-filling port 62b, solvent which has been degassed (exposure to the lowered pressure of a laboratory aspirator is sufficient) is introduced through the cell-filling port 62b from a syringe and needle (not shown) completely filling the interrogation chamber 61b. The cell-filling port 62b is then fitted with the cell-filling-port stopper 63; it is preferable that all air be excluded from the interrogation chamber 61b during the seating of the stopper 63.

Interrogation cell fitted to the cell block 3 which are intercalated between two semipermeable membranes, as exemplified by upper interrogation cell 58' of cell-block-component embodiment 101 intercalated between semipermeable membranes 66, are also charged with macro-ion samples prior to fitting the cell block 3 to the lower instrument assembly 2b. Typically, the macro-ion samples are solutions of macro-ions exhaustively dialyzed against the solvent to be used in the electrophoretic steady-state analysis of the macro-ion samples. The interrogation chamber of each single-chamber interrogation cell, fitted to the cell block 3, which is intercalated between two semipermeable membranes, as exemplified by interrogation chamber 90 of interrogation cell 87 intercalated between upper and lower semipermeable membranes 92 and 92' in cell-block-component embodiment 100, is filled with macro-ion solution following the solvent-charging procedure described above for filling the reference interrogation chambers of double-chamber interrogation cells with solvent, as represented by the filling of interrogation chamber 61b of interrogation cell 58. Similarly, the second interrogation chamber of each double-chamber interrogation cell, fitted to the cell block 3, which is intercalated between two semipermeable membranes (i.e., the interrogation chamber not charged with solvent as described above), as represented by interrogation chamber 61a' of upper interrogation cell 58' intercalated between semipermeable membranes 66 in cell-block-component embodiment 101, is filled with macro-ion solution following the solvent-charging procedure described above for charging reference interrogation chambers of double-chamber interrogation cells with solvent, as represented by the filling of interrogation chamber 61b of interrogation cell 58. The interrogation chamber of each double-chamber interrogation cell fitted to the cell block 3 which is filled with a macro-ion solution sample, as represented by interrogation chamber 61a of interrogation cell 58, and the interrogation chamber of single-chamber interrogation cells, as represented by interrogation chamber 90 of interrogation cell 87, are designated macro-ion interrogation chambers. During the macro-ion solution charging procedure, it is preferable that all air be excluded from each macro-ion interrogation chamber, as represented by interrogation chamber 61a' of upper interrogation cell 58', when the cell-filling-port stopper 63 is seated after the macro-ion solution has been introduced. The macro-ion interrogation chamber of each interrogation cell fitted to cell block 3, as exemplified by interrogation chamber 61a' of upper interrogation cell 58' fitted to cell-block-component embodiment 101, are always aligned coextensively with the rectangular holes 82a and 82b of the respective upper and lower cell-block assemblies 74a and 74b.

Single interrogation cells fitted to the cell block 3 which are adjacent to only one semipermeable membrane, as exemplified by interrogation cell 58 and semipermeable membrane 66 of cell-block-component embodiment 99, are charged with macro-ion solution at a later stage (see below).

The cell block 3 is next seated into the lower cell-block compartment 23b. When so seated, the cell block 3 is oriented with the reference interrogation chambers of the double-chamber interrogation cells present in the cell block 3, as exemplified by interrogation chamber 61b of interrogation cell 58 fitted to cell-block-component embodiment 99, positioned between the macro-ion interrogation chambers of the interrogation cells, as exemplified by interrogation chamber 61a of interrogation cell 58, and the right lateral wall 13b of the lower cell-block compartment 23b; when single-chamber interrogation cells, as exemplified by interrogation cell 87 of cell-block-component embodiment 100, are present in the cell block 3, the support post of the lower cell-support piece, as represented by support post 89 of lower cell-support piece 93b, is positioned between the macro-ion interrogation chambers of the interrogation cells, as exemplified by interrogation chamber 90 of interrogation cell 87, and the right lateral wall 13b of the lower cell-block compartment 23b. This choice between two possible orientations of the cell block 3 is arbitrary; however, a consistent protocol for the placement of the cell block 3 into the lower cell-block compartment 23b is preferred in order to align the instrument 1 properly each time in the optical system, as represented by Rayleigh optical system 115 (see below) employed to interrogate the interrogation cells, as exemplified by interrogation cell 87, fitted to the instrument 1. The upper instrument assembly 2a is now secured to the lower instrument assembly 2b with the bolts 4, washers 6, and nuts 5.

With the upper and lower sample-loading-port toppers 47a and 47b seated in the respective upper and lower sample-loading-port fittings 43a and 43b and the gas-tower caps 27 removed, solvent which has been degassed (exposure to the lowered pressure of a laboratory aspirator is sufficient) is now introduced into the instrument 1 through the gas towers 24a and 24b. To facilitate the venting of air as the solvent enters the lower inner chamber 20b, a blunt-tipped, conventional syringe needle (not shown) is inserted through the self-sealing valve 53 located in the front wall 15b of the lower instrument assembly 2b; the needle is removed when the lower inner chamber 20b is nearly filled with solvent. Valves of alternative designs which facilitate the venting of air from the lower inner chamber 20b during the solvent filling procedure may be substituted for self-sealing valve 53. Solvent is added until the solvent menisci 106a and 106b are to within a centimeter of the respective collars 25a and 25b of the respective gas towers 24a and 24b; the gas-tower caps 27 are then fitted to the gas towers 24a and 24b.

At this point, air bubbles trapped in the instrument 1, except those contained within the gas towers 24a and 24b, are removed (bubbles can cause distortions in the geometry of the directed electrical field, especially any remaining in the cell block 3). The majority of the bubbles are removed by physically lifting and then rotating the instrument 1 clockwise one or two complete revolutions about a horizontal axis normal to and intersecting the front walls 15a and 15b of the instrument 1. This rotation procedure causes air bubbles to be carried up into the gas towers 24a and 24b. Bubbles which sometimes remain in the cell block 3 after completion of the rotation procedure are dislodged with a jet of solvent expressed from a large syringe and long needle (not shown) with the needle inserted through either sample-loading port, as represented by lower sample-loading port 41b, with the relevant sample loading-port stopper, as represented by lower sample-loading-port stopper 47b, temporarily removed for the duration of this bubble-dislodging procedure. To avoid solvent spillage from the lower sample-loading port 41b during the bubble-dislodging procedure, the instrument 1 is inverted prior to the removal of the lower sample-loading-port stopper 47b; and to avoid solvent spillage from the upper sample-loading port 41a during the bubble-dislodging procedure, the gas-tower cap 27 is removed from the gas tower 24a and the solvent present in the gas tower 24a is extracted with a large syringe and needle (not shown) prior to the removal of the upper sample-loading-port stopper 47a. The air bubbles thus dislodged from the cell block 3, are carried up into the gas towers 24a and 24b by a repetition of the rotation procedure described formerly. When air bubbles have been substantially eliminated from the instrument 1 (except for the air present above the solvent menisci 106a and 106b), solvent is added or removed from the open gas towers 24a and 24b with a syringe and needle (not shown) to establish the desired levels for the solvent menisci 106a and 106b (FIG. 12a). In selected electrophoretic steady-state analyses, the extension tube 30 is attached to a gas tower, as exemplified by gas tower 24a, in order that the desired difference in the levels of the solvent menisci 106a and 106b can be achieved (see below). After the solvent menisci 106a and 106b are established at the desired levels, the gas-tower caps 27 are secured to the gas towers 24a and 24b, or to one gas tower, as exemplified by gas tower 24a, and the extension tube 30, if attached as described.

When the cell block 3 is fitted with a cell-block-component embodiment featuring one interrogation cell and one semipermeable membrane, as represented by interrogation cell 58 and semipermeable membrane 66 fitted to cell-block-component embodiment 99, the macro-ion interrogation chamber, as represented by interrogation chamber 61a of interrogation cell 58, is charged with a macro-ion sample at this juncture. The procedure for charging the macro-ion interrogation chamber, as represented by interrogation chamber 61a, with macro-ion sample is illustrated below by the charging procedure followed in so charging interrogation chamber 61a of interrogation cell 58 of cell-block-component embodiment 99 fitted to the instrument 1 (FIG. 3a): A blunt-tipped syringe needle 108 fitted to a syringe 107 charged with macro-ion solution is inserted through the self-sealing valve 49 located in the upper sample-loading-port stopper 47a; the needle 108 passes through the upper partition slot 22a, the upper cell-block assembly 74a, and reaches a point just above the semipermeable membrane 66. Next, a small volume of macro-ion solution (typically 0.1–0.6 milliliters) is expressed from the needle 108. Because the density of the macro-ion solution is greater than the density of the solvent (but see below), the macro-ion sample layers on the semipermeable membrane 66 surface, but typically does not fill the interrogation chamber 61a (see below). Chilling the syringe 107 loaded with the macro-ion solution to a temperature below that of the solvent present in the instrument 1 (if possible), prior to the charging procedure, facilitates the deposition of an evenly distributed layer of the macro-ion solution on the surface of semipermeable membrane 66. After the deposition of the macro-ion solution, the syringe needle 108 is withdrawn from the instrument 1 with care taken not to allow additional macro-ion solution to be expressed from the syringe needle 108. The cell 87 of the cell-block-component embodiment 100 may also be charged with a macro-ion sample as just described if the semipermeable membrane 92 is replaced with a cell gasket (not shown) similar in design to the cell gasket 64 of the cell-block-component embodiment 99 but having the exterior dimensions of the semipermeable membrane 92. Connectors of alternative designs capable of being sealed and which allow the syringe needle 108 to be inserted through the upper sample-loading port 41a (or through sample-loading port 41b; see below) may be substituted for self-sealing value 49.

Figure 1C:
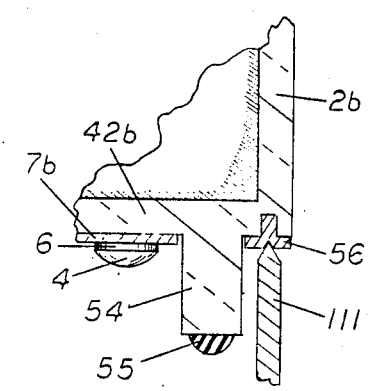
FIG. 1c is a fragmentary, front, sectional view of the preferred embodiment.
Figure 2A:
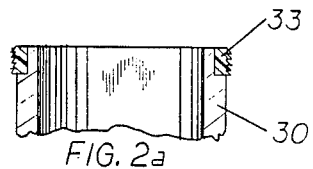
FIG. 2a is a fragmentary, cross-sectional view of the upper end of the extension tube, which may be attached to the preferred embodiment.
Figure 2B:
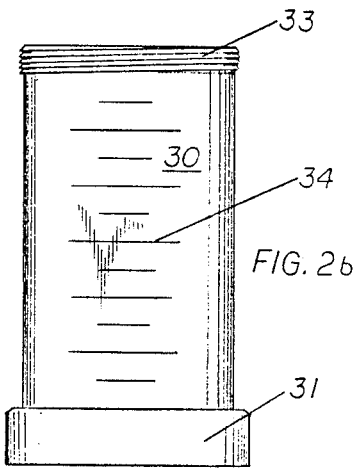
FIG. 2b is a side view of the extension tube.
Figure 2C:
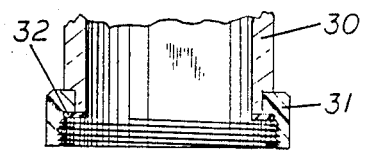
FIG. 2c is a fragmentary, cross-sectional view of the lower end of the extension tube.

When the instrument 1 is charged with solvent and macro-ion sample(s), it is ready for a macro-ion analysis, which together with the solvent analysis to follow comprise the instrumental complement of an electrophoretic steady-state analysis: The instrument 1 is first aligned in an ppropriate optical system, as exemplified by Rayleigh interference optical system 115, which is housed in a complete instrument assembly specifically designed for carrying out electrophoretic steady-state analyses; said instrument assembly is hereafter in this section of the present disclosure also referred to as the instrument complex, as exemplified by instrument complex 129 (FIG. 10). The instrument 1 is placed on a precision mount (not shown) located in the thermostatted housing of the instrument complex, as exemplified by thermostatted housing 116 of instrument complex 129; the mount pins 111 of the precision mount engage the four, dimpled, mount studs 56 on the bottom wall 42b of the instrument 1 (FIG. 1c). The precision mount aligns the instrument 1 in an optical system fitted to the instrument complex, as represented by Rayleigh interference optical system 115 of instrument complex 129, for the purpose of interrogating the contents of the interrogation cell(s) fitted to the instrument 1, as exemplified by interrogation cell 58 of cell-block-component embodiment 99.

The Rayleigh interference optical system 11 fitted to the instrument complex 129 features an optical energy (light) source 118 capable of producing intense optical energy in the visible wavelength range. The intense optical energy is collimated by a very narrow light-source slit 119 before passing through a narrow band-pass optical filter 120 (the band centered about a wavelength in the visible spectrum), a collimating lens 121, and a Rayleigh interference double-slit mask 122 whose slits are disposed vertically. The two resulting, essentially monochromatic parallel beams of optical energy aligned along the axes 113a and 113b proceed from the double-slit mask 122 and pass through the cell block 3 of the instrument 1.

The beam of optical energy aligned along the axis 113a passes through the macro-ion interrogation chamber of each interrogation cell, as represented by interrogation chamber 61a of interrogation cell 58, fitted to the instrument 1; the beam of optical energy aligned along the axis 113b passes through the reference interrogation chamber of each double-chamber interrogation cell, as represented by interrogation chamber 61b of interrogation cell 58, fitted to the instrument 1. If the instrument 1 is fitted with single-chamber interrogation cells, as exemplified by interrogation cell 87, the beam of optical energy aligned along the axis 113b passes through the reference-beam channel, as represented by reference-beam channel 132 of lower cell-support piece 93b; the beam of optical energy aligned along the axis 113b, therefore, does not intersect any physical element of the instrument 1. In addition, the beam of optical energy aligned along the axis 113b passes through the adjustable optical-path compensator 130 (see, for instance, Born, M. and Wolf, E. (1975), *Principles of Optics*. New York, NY, Pergamon Press, p. 270) positioned at a point between the instrument 1 and a condensing lens 123; however, if double-chamber interrogation cells, as exemplified by interrogation cell 58 of cell-block-component embodiment 99 are fitted to the instrument 1, the adjustable optical-path compensator, as exemplified by adjustable optical-path compensator 130, is removed from the path of the beam of optical energy of the Rayleigh interference optical system, as exemplified by Rayleigh interference optical system 115, aligned along the axis 113b.

After passing through the condensing lens 123, the beams of optical energy aligned along the axes 113a and 113b pass through a "camera" lens 125 and a cylindrical lens 126 before converging on an automated image analyzer 127 (e.g., a precision photodiode array), which in this instance takes the place of the camera frequently fitted at this point to Rayleigh interference optical systems employed in prior art analytical instruments; three front-surface mirrors 124 are placed at strategic points to confine the optical path of the optical system 115 to convenient dimensions. It is contemplated that electrical leads 128 connected to the automated image analyzer 127 would convey digitized records of the optical images analyzed by the automated image analyzer 127 to an external computer (not shown) for further analysis. A light-proof housing 117 covers the instrument complex 129.

Several components which would be present in a complete instrument assembly specifically designed for making electrophoretic steady-state analyses including refrigeration and temperature regulatory units have been omitted from the schematic representation of the instrument complex 129 depicted in FIG. 10. It would also be possible to fit the instrument complex, as represented by instrument complex 129, with either a single-beam (not shown) or a dual-beam absorption optical system (not shown) or other optical system capable of quantitatively interrogating the contents of the interrogation cell(s) fitted to the instrument 1, as represented by interrogation cell 58 of cell-block-component embodiment 99.

After the instrument 1 is placed on the precision mount (not shown) in the instrument complex, as exemplified by instrument complex 129, each self-sealing valve 29 located in the gas-tower caps 27 is engaged by a blunt-tipped, conventional syringe needle 110 which is secured into the end of a gas-venting tube 109 (e.g., of polyethylene); the gas-venting tubes 109 vent to the outside of the instrument complex, as exemplified by instrument complex 129. Connectors of alternative designs capable of being sealed and which allow the gas-venting tubes 109 to be coupled to the gas towers 24a and 24b may be substituted for the self-sealing valves 29.

The female electrical jacks 40a and 40b, are engaged by electrical leads 52a and 52b fitted with conventional male electrical jacks (not shown). The electrical leads 52a and 52b provide direct electrical current to the instrument 1 from a direct-current, continuously adjustable electrical power source which is an integral element of the instrument complex, as exemplified by electrical power source 96 of instrument complex 129. The electrical power source, as represented by electrical power source 96, is capable of delivering a constant electrical current over a continuous range of 0 to approximately 10 milliamperes at a maximum voltage of approximately 30 volts to each instrument 1 to which it is connected. To initiate the macro-ion analysis, a potential difference is applied across the electrodes 35a and 35b by means of the electrical power source, as exemplified by electrical power source 96, to establish a predetermined electrical current flow through the instrument 1 (see below). The polarity of the potential difference applied to electrodes 35a and 35b is determined by the sign of the net charge carried by the macro-ions present in the instrument 1 and the preferred direction (up or down) of the macro-ion concentration gradient(s)

which form at electrophoretic steady state (discussed below).

After the macro-ions present in the instrument 1 have achieved electrophoretic steady state, usually within an 8-36-hour time span after the directed electrical field is first applied (see below), an optical recording is made of the concentration gradient(s) of the macro-ions with the optical system, as represented by Rayleigh interference optical system 115 of instrument complex 129, within which the instrument 1 is aligned. The acquisition of the optical recording of the macro-ions maintained at electrophoretic steady state within the instrument 1 marks the end of the instrumental component of a macro-ion analysis.

The solvent analysis is carried out next, at the end of which a second optical recording is made. When the instrument 1 is fitted with a single interrogation cell adjacent to a single semipermeable membrane, as exemplified by interrogation cell 58 and semipermeable membrane 66 of cell-block-component embodiment 99, the solvent analysis is relatively simple: The instrument 1 is removed from the instrument complex, as represented by instrument complex 129, and the macro-ion sample is extracted from the macro-ion interrogation chamber, as represented by interrogation chamber 61a of interrogation cell 58, with the syringe 107 and needle 108. The needle 108 is inserted through the self-sealing valve 49 located in the upper sample-loading-port stopper 47a as described in the relevant macro-ion charging procedure above. The withdrawal of several milliliters of liquid with the needle 108 tip positioned close to the semipermeable membrane surface, as exemplified by the upper surface of semipermeable membrane 66, is usually sufficient to remove the last traces of the macro-ions from the interrogation cell, as exemplified by interrogation cell 58. The instrument 1 is then replaced in the instrument complex, as exemplified by instrument complex 129. After 1-2 hours, during which the instrument 1 is maintained under the same conditions of electrical field and temperature as were observed in the macro-ion analysis, the second (solvent analysis) optical recording is made.

When more than one interrogation cell is fitted to the instrument 1, as exemplified by the utilization in the instrument 1 of upper, middle, and lower interrogation cells 58', 58'', and 58''' of cell-block-component embodiment 100, or when one interrogation cell intercalated between two semipermeable membranes is fitted in the instrument 1, as represented by the utilization in the instrument 1 of interrogation cell 87 and upper and lower semipermeable membranes 92 and 92' of cell-block-component embodiment 100, the procedure for the solvent analysis is as follows: With the gas-tower caps 27 removed, the bulk of the solvent within the solvent chambers 133a and 133b and the gas towers 24a and 24b is drained from the gas towers 24a and 24b. The upper and lower instrument assemblies 2a and 2b are then disengaged, and the cell block 3 is removed from the lower instrument assembly 2b. After the cell-filling-port stopper 63 is removed from the cell-filling port of each macro-ion interrogation chamber present in the instrument 1, as represented by cell-filling port 91 and interrogation chamber 90 of interrogation cell 87 fitted to cell-block-component embodiment 100, the macro-ion solution is extracted with a syringe and needle (not shown) from each macro-ion interrogation chamber, as represented by interrogation chamber 90. After several rinses with solvent, each macro-ion interrogation chamber, as exemplified by interrogation chamber 90, is filled with solvent and stoppered following the solvent-charging procedure described above for charging the reference interrogation chambers of double-chamber interrogation cells, as exemplified by interrogation chamber 61b of interrogation cell 58, with solvent. The instrument 1 is then reassembled, recharged with solvent as described earlier, and replaced on the precision mount (not shown) of the instrument complex, as represented by instrument complex 129. An optical recording is then made 1-2 hours after the instrument 1 has been maintained under the same conditions of temperature and electrical field as were observed in the macro-ion analysis.

It has been found that the optical records of a typical solvent analysis made before and after the 1-2-hour incubation period often do not exhibit detectable differences; nevertheless, it is preferable that the relevant protocol for the solvent analysis be followed each time, particularly when unfamiliar solvent systems are employed. After the optical record of the solvent analysis is obtained, the instrument 1 is removed from the instrument complex, as exemplified by instrument complex 129; the gas-tower caps 27 are then removed, the bulk of the solvent is drained from the instrument 1 through the gas towers 24a and 24b, and the instrument 1 is disassembled and cleaned. All components of the preferred embodiment 1 are designed for repeated use with the exception of semipermeable membranes and cell gaskets, as exemplified by semipermeable membrane 66 and cell gasket 64.

The optical records from the macro-ion and solvent analyses carried out in the preferred embodiment 1 are analyzed by mathematical procedures similar to those currently employed to analyze the optical records encountered in the prior technique of equilibrium ultracentrifugation (see description of electrophoretic steady-state theory, below). As discussed earlier, it is contemplated that the superior quality of the optical images which can be obtained with the apparatuses of the present invention will make it possible to digitally record the optical images with automated image-analysis techniques. With these records fed directly into a computer, the analysis of the optical data as prescribed by electrophoretic steady-state theory can be largely automated as well.

Several experimental parameters encountered in the operation of the preferred embodiment 1 are more easily understood within the context of electrophoretic steady-state theory. Accordingly, a hypothetical electrophoretic steady-state analysis carried to the point at which the macro-ions achieve electrophoretic steady state during the macro-ion analysis is briefly described, followed by a mathematical description of the analysis based on electrophoretic steady-state theory. This is followed, in turn, by a mathematical development of additional aspects of the theory. Finally, several design features of the preferred embodiment 1 are discussed which are desirable for the fulfillment of several objects and purposes of the present invention.

For the aforesaid hypothetical analysis, the instrument 1 is fitted with the cell-block-component embodiment 99. The instrument 1 including the reference interrogation chamber 61b of the interrogation cell 58 is charged with solvent following the relevant procedures described above. The solvent is comprised of a dilute, pH-buffered, aqueous solution of a simple inorganic salt (e.g., KCl). It is assumed that the semipermeable membrane 66 fitted to the cell-block-component embodiment 99 is fabricated from cellulosic (dialysis) film (e.g., Spectra/Por 1). Semipermeable membranes fabricated from cellulosic film typically do not exhibit significant bulk solvent flow under the mild osmotic pressures encountered in electrophoretic steady-state analyses (see below); accordingly, the solvent menisci 106a and 106b are set at approximately the mid-points of the respective gas towers 24a and 24b. Next, a solution of monodisperse macro-ions 112 in dialysis equilibrium with the aforesaid solvent is introduced into the macro-ion interrogation chamber 61a just above the upper surface of the semipermeable membrane 66 (FIG. 11a) with the syringe 107 and needle 108 following the relevant procedure described earlier (it is assumed that the vectors of the concentration and density gradients of the macroions 112 established at electrophoretic steady state are directionally identical; see below).

The instrument 1 is next placed on the precision mount (not shown) of an instrument complex specifically designed to carry out electrophoretic steady-state analyses, as exemplified by instrument complex 129. An electrical potential difference applied across the electrodes 35a and 35b from the electrical power source, as represented by electrical power source 96, establishes a stable, directed electrical field 114 (arrow; FIG. 11b) within the macro-ion interrogation chamber 61a which is linear and uniform above the semipermeable membrane 66 (see below); the directed electrical field 114 is supported by the solvent ions, all of which are able to pass through the semipermeable membrane 66. The polarity of the potential difference causes the macro-ions 112, which possess a net positive charge, to migrate in the direction of the semipermeable membrane 66. Because the macro-ions 112 are stopped by the semipermeable membrane 66, the local concentration of the macro-ions 112 at the semipermeable membrane 66 surface increases, and the micro-ion 112 concentration gradient thus formed produces a diffusion-driven back flow of the macro-ions 112. In time, the macro-ion 112 concentration gradient stabilizes (i.e., becomes substantially static and substantially unchanging) as electrophoretic steady state is achieved; at every point in the macro-ion 112 concentration gradient, the macro-ion 112 flow due to electrophoresis is countered, exactly, by the macro-ion 112 flow due to diffusion (FIG. 11b). It is assumed that the concentration gradient of the macroions 112 stabilized at electrophoretic steady state attenuates to infinite dilution within the macro-ion interrogation chamber 61a (i.e., a complete, as opposed to a "truncated", concentration gradient of the macro-ions 112 is formed within the macro-ion interrogation chamber 61a; see below).

It is to be noted that although the semipermeable membranes fitted to the instrument 1, as exemplified by semipermeable membrane 66, cover both the macro-ion and the reference interrogation chambers of the double-chamber interrogation cells fitted to the cell block 3, as exemplified by interrogation chambers 61a and 61b of interrogation cell 58, the reference interrogation chambers, as represented by interrogation chamber 61b, are substantially insulated, electrically, from the imposed directed electrical fields, as exemplified by directed electrical field 114, applied to the instrument 1. Thus, the directed electrical fields within the instrument 1, as represented by directed electrical field 114, are supported by the flow of the solvent ions between the electrodes 35a and 35b via: the outer chambers 16a and 16b; the upper and lower partition slots 22a and 22b; the upper inner and lower inner chambers 20a and 20b; the rectangular holes 82a and 82b of the respective cell-block assemblies 74a and 74b; the rectangular cutouts 83a in the soft-rubber components 72 and the rectangular holes 73 in the thinner components 71 of the compound gaskets 70; the rectangular holes in the upper and lower cell-support pieces, as exemplified by rectangular holes 68a and 68b of respective upper and lower cell-support pieces 67a and 67b; the rectangular hole in the cell gasket (if present), as represented by rectangular hole 65 of cell gasket 64; the semipermeable membrane(s), as represented by semipermeable membrane 66; and the macro-ion interrogation chamber(s), as exemplified by interrogation chamber 61a, fitted to the instrument 1. Accordingly, the contents of the macro-ion interrogation chambers, as exemplified by interrogation chamber 61a of interrogation cell 58, but not the contents of the reference interrogation chambers, as exemplified by interrogation chamber 61b of interrogation cell 58, fitted to the instrument 1 are exposed to the imposed directed electrical fields, as represented by directed electrical field 114, applied to the instrument 1.

Because the semipermeable membrane 66 offers negligible resistance to the solvent ions and their electrophoretic migration rates are small, no experimentally significant concentration gradients of the solvent ions are formed against the semipermeable membrane 66. Accordingly, except for minor adjustments required to maintain electroneutrality, the concentrations of the solvent ions throughout the macro-ion interrogation chamber 61a remain substantially unchanged during and after the formation of the macro-ion 112 concentration gradient stabilized at electrophoretic steady state. Moreover, experimentally significant temperature gradients are absent from the macro-ion interrogation chamber 61a due to the very low wattage levels required to support macro-ion concentration gradients at electrophoretic steady state, as represented by the macro-ion 112 concentration gradient, under typical macro-ion analysis conditions. Thus, the thermodynamic system whose boundaries minimally encompass the macro-ion 112 concentration gradient stabilized at electrophoretic steady state within the macro-ion interrogation chamber 61a is essentially isothermal and of substantially constant composition over time. Nevertheless, the thermodynamic system is not in thermodynamic equilibrium; the continuing migration of the solvent ions through the thermodynamic system generates an entropic flow, however negligible, to the environment. Rather, the thermodynamic system is in steady state and is appropriately described by irreversible thermodynamic theory.

The slow migration rates of the ionic species present in the macro-ion interrogation chamber 61a which are generated by the imposed directed electrical field 114 and the low concentrations of the ionic species ensure that the flows of the ionic species are adequately described by linear summations of conjugate and coupled flow terms written in the standard Onsager phenomenological notation. Because the semipermeable membrane 66 fitted to the instrument 1 has been assumed to be fabricated from cellulosic film, bulk solvent flow through the semipermeable membrane 66 due to osmotic pressure (see below) is experimentally insignificant during the macro-ion analysis, and water flow due to water-of-hydration can be assumed to be negligible when solvents containing simple salts (e.g., KCl) are used. Consequently, only ionic flows need be considered in the mathematical description of the macro-ion analysis. As will be described in greater detail below, the design of the preferred embodiment 1 causes the directed electrical field 114 to be substantially linear and substantially perpendicular to the surfaces of the semipermeable membrane 66 fitted to the instrument 1 when the electrical potential difference is applied to the electrodes 35a and 35b. Accordingly, the flows of the ionic species (including the macro-ion 112 back flow due to diffusion) within the macro-ion interrogation chamber 61a are substantially unidimensional and substantially perpendicular to the surfaces of the semipermeable membrane 66 as well.

For the ionic species present in the macro-ion interrogation chamber 6a, the total flow is:

$$J_t = J_m + \sum_j J_j = L_{mm}\vec{F}_m + \sum_j L_{mj}\vec{F}_j + \sum_j \sum_k L_{jk}\vec{F}_k \quad (1)$$

where the L's are the phenomenological coefficients, the F's are the driving forces, k indexes all ionic species, j indexes the solvent ions only, and m refers to the macro-ions 112. The flow of the macro-ions 112, alone, is then:

$$J_m = L_{mm}\vec{F}_m + \sum_j L_{mj}\vec{F}_j \quad (2)$$

The Nernst-Planck equation (see, for instance, Bockris, J. O'M., and Reddy, A. K. N. (1970), *Modern Electrochemistry*, Vol. 1, Chpt. 4, New York, N.Y., Plenum Press) describes the flow of a charged species in an electrochemical gradient in the absence of other ions and may be substituted into equation 2 to define the conjugate term at any point in time:

$$J_m = -\frac{C_m}{N_A^+ m}\left(\frac{\partial \bar{\mu}}{\partial x}\right) + \sum_j L_{mj}\vec{F}_j \quad (3a)$$

$$J_m = -\frac{C_m}{N_A^+ m} Fz_m\left(\frac{\partial \chi}{\partial x}\right) - \frac{C_m}{N_A^+ m}\left(\frac{\partial \mu}{\partial x}\right) + \sum_j L_{mj}\vec{F}_j \quad (3b)$$

where $C_m$ is the molar concentration of the macro-ions 112, $f_m$ is the frictional coefficient of the macro-ions 112 at macro-ion 112 concentration $C_m$, F is Faraday's constant, $N_A$ is Avogadro's number, $z_m$ is the charge number carried by the macro-ions 112, x is the axis of the ionic flows (perpendicular to the surfaces of the semipermeable membrane 66), $\partial \bar{\mu}/\partial x$ is the total (electrochemical) potential gradient, and $\partial \omega/\partial x$ and $\partial \mu/\partial x$ are the electrostatic and chemical potential gradients, respectively. $C_m/N_A f_m$ will be recognized as the phenomenological coefficient, $Fz_m(\partial \omega/\partial x)$ and $\partial \mu/\partial x$ as the two driving forces of the conjugate term, and $-\partial \omega/\partial x$ as the directed electrical field 114.

Even at modest concentrations, the presence of solvent ions in the macro-ion interrogation chamber 61a can substantially reduce the mobility of the macro-ions 112 to a value below the mobility of the macro-ions 112 in the absence of other ions. Several mechanisms have been identified, notably the electrophoretic and relaxation effects, by which the flows of different ionic species interact to cause significant decreases in the local electrical fields experienced by the individual ions. These effects on the macro-ion 112 flow are expressed by the coupled flow terms of equations 3a and 3b.

When the electrical potential difference is first applied to the electrodes 35a and 35b, the macro-ion 112 flow near the upper surface of the semipermeable membrane 66 is defined substantially by the first and third terms of the right-hand side of equation 3b. Soon, however, the second term of the right-hand side of equation 3b is also required to define the flow of the macro-ions 112 as the macro-ion 112 build-up at the upper surface of the semipermeable membrane 66 initiates a diffusion-driven counter flow. Over time, the macro-ion 112 concentration gradient grows causing the back flow of macro-ions 112 to increase. As a result, the net flow of the macro-ions 112 progressively slows, and finally, macro-ion 112 transport ceases altogether at every point in the macro-ion interrogation chamber 61a as a well-defined, stable and substantially unchanging concentration gradient of the macro-ions 112 forms and electrophoretic steady state is achieved (FIG. 11b). After setting $J_m$ equal to zero and rearranging, equation 3b becomes:

$$0 = Fz_m\left(\frac{\partial \chi}{\partial x}\right) + \frac{\partial \mu}{\partial x} - \frac{N_A^+ m}{C_m}\sum_j L_{mj}\vec{F}_j \quad (4)$$

The chemical potential gradient in equation 4 can be written as the sum of its dependencies on temperature, pressure, and composition:

$$\frac{\partial \mu}{\partial x} = \left(\frac{\partial \mu}{\partial T}\right)_{P,C_m}\left(\frac{\partial T}{\partial x}\right) + \quad (5a)$$

$$\left(\frac{\partial \mu}{\partial P}\right)_{T,C_m}\left(\frac{\partial P}{\partial x}\right) + \left(\frac{\partial \mu}{\partial C_m}\right)_{P,T}\left(\frac{\partial C_m}{\partial x}\right).$$

Because no pressure gradients are present in the macro-ion 112 concentration gradient stabilized at electrophoretic steady state and the contents of the macro-ion interrogation chamber 61a are assumed to be essentially isothermal, equation 5a reduces to the familiar expression for the diffusional force in terms of the concentration gradient:

$$\frac{\partial \mu}{\partial x} = \frac{RT}{C_m}\left(\frac{\partial C_m}{\partial x}\right)(1 + C_m \partial(\ln f_m)/\partial C_m) \quad (5b)$$

where $f_m$ is the activity coefficient of the macro-ions 112 (molar scale), R is the gas constant, and T is the absolute temperature. Substituting equation 5b into equation 4, replacing $\partial \omega/\partial x$ with the equivalent quantity, $-E/300$ (E is measured in conventional volts per centimeter), and further rearranging yields:

$$\frac{300 RT}{EC_m}\left(\frac{dC_m}{dx}\right) = \quad (6)$$

$$\frac{Fz_m}{(1 + C_m \partial(\ln f_m)/\partial C_m)}\left(1 + \frac{300 N_A^+ m}{Fz_m EC_m}\sum_j L_{mj}\vec{F}_j\right)$$

(Because $C_m$ is no longer time-dependent, total differentials are appropriate in equation 6). Equation 6 measures the apparent molar (net) charge of the macro-ions 112 plus a quantity which includes the coupled flow terms (i.e., the effects of solvent ion-macro-ion 112 interactions upon the flow of the macro-ions 112). At the low molar ratios of macro-ion-to-total solvent ion encountered in electrophoretic steady-state analyses (typically within a range of 0.0001 to 0.01), the values of the phenomenological coefficients of the coupled flow terms, $L_{mj}$'s, are substantially dependent upon the first power of the macro-ion 112 concentration; consequently, the second term within the parentheses of equation 6 is substantially constant for all values of $C_m$ within the macro-ion 112 concentration gradient. This term is also typically negative.

A new quantity--the molar diminished charge of the macro-ions 112--may be introduced here, $$Fz'_m = Fz_m \left( 1 + \frac{300 \, N_A^+{}_m}{Fz_m E C_m} \sum_j L_{mj} \vec{F}_j \right) \quad (7)$$

which when substituted into equation 6 (and converting to units of mass concentration) yields an expression defining the apparent molar diminished charge of the macro-ions 112:

$$\frac{300 \, RT}{E c_m} \left( \frac{dc_m}{dx} \right) + \quad (8)$$

$$Fz'_m / (1 + c_m \partial(\ln y_m)/\partial c_m) = Fz'_{m,app}$$

where $c_m$ is in grams/liter and $y_m$ is the activity coefficient of the macro-ions 112 in mass units. The physical-chemical meaning of $Fz'_m$ becomes clear when equation 7 is substituted into equation 3b (noting that $\partial \omega / \partial x = -E/300$):

$$J_m = -\frac{C_m}{N_A^+{}_m} \left[ Fz'_m \left( \frac{\partial \chi}{\partial x} \right) + \frac{\partial \mu}{\partial x} \right] \quad (9)$$

$Fz'_m$ is thus the molar net charge which the macro-ions 112 would be required to carry in order that they have the same electrophoretic mobility in the absence of the solvent ions as the macro-ions 112 (in reality) exhibit in the presence of the solvent ions. In a looser sense, $Fz'_m$ may be viewed as the net charge of the solvent-ion-macro-ion 112 complexes which move in response to the directed electrical field 114 and diffusion.

The molar diminished charge is a quantity of particular interest to the polyelectrolyte chemist because the difference between the molar (actual) charge and the molar diminished charge of a macro-ionic species in the presence of small ions is a direct, experimental measure of the interactions between the macro-ionic species and small ions which Debye-Hückel and other electrostatic potential theories attempt to model (see, for instance, Tanford, C. (1961), *Physical Chemistry of Macromolecules*, Chpts. 6 and 7, New York, N.Y., Wiley & Sons).

A number of expressions based on electrostatic potential theory have been developed to describe the flow of macro-ions in an electrical field in which the reduced electrical field experienced by the macro-ions is defined by measurable quantities. One such expression due to Henry for the flow of a spherical macro-ionic species can take the form:

$$J_m = \frac{C_m E}{300 N_A^+{}_m} \left[ \frac{Fz_m X(\kappa R_m)}{1 + \kappa R_m} \right] \quad (10a)$$

where $R_m$ is the radius of the macro-ionic species, $X(\kappa R_m)$ is Henry's function (dimensionless and having a value between 1.0 and 1.5), and $\kappa$ is the Debye-Hückel constant:

$$\kappa = \left[ \frac{8\pi N_a e^2}{1000 D k T} \right]^{\frac{1}{2}} I^{\frac{1}{2}} \quad (10b)$$

in which e is the charge on an electron, D is the dielectric constant of the solvent, k is Boltzmann's constant, and I is the ionic strength of the solvent. From equation 9, it can be seen that $Fz'$ is equivalent to the bracketed expression in equation 10a.

Equation 8 may be rewritten with the nonideality term expressed as the familiar virial expansion in macromolecular concentration:

$$\phi \left( \frac{d(\ln c_m)}{dx} \right) = \frac{Fz'_m}{(1 + 2B'Fz'_m c_m + \ldots)} = Fz'_{m,app} \quad (11)$$

where B' is the second virial coefficient (comparable, but not equal, to the colligative second virial coefficient); higher virial terms can be assumed to be negligible for the vast majority of aqueous macro-ion systems within the macro-ion concentration range typically encountered in electrophoretic steady-state analyses. $\phi = 300RT/E$, and $dc_m/c_m dx$ is replaced by the equivalent quantity, $d(\ln c_m)/dx$. Equation 11 is similar in form to the primary equation of the prior theory of equilibrium ultracentrifueguation for measuring molecular weights (accordingly, both equations measure the apparent weight-average moment). The two equations, however, differ in a major respect: In the equilibrium ultracentrifugation equation, the logarithm of the macromolecular concentration is differentiated with respect to the square of the radial distance in the ultracentrifuge rotor; in the electrophoretic steady-state equation, the logarithm of the macro-ion 112 concentration is differentiated with respect to the first power of x. This difference arises because the centrifugal field is radially dependent, whereas, the directed electrical field 114 is linear.

All quantities on the left side of equation 11 are either known constants or can be independently measured. T is the environmental temperature of the instrument 1. The macro-ion 112 concentration gradient stabilized at electrophoretic steady state can be accurately recorded by an appropriate optical system, as represented by Rayleigh interference optical system 115 of instrument complex 129 (see below); the optical recording of the gradient is analyzed by mathematical procedures similar to those currently employed to analyze macromolecular concentration gradients encountered in the prior technique of equilibrium ultracentrifugation. Ohm's law allows the directed electrical field 114 to be expressed as the ratio of the total current density to the conductivity:

$$E = \sum_k i_k / \sum_k \kappa_k = \left(i_m + \sum_j i_j\right) / \left(\kappa_m + \sum_j \kappa_j\right) \quad (12)$$

$$= \left(i_m + \sum_j i_j\right) / \left(i_m/E + \sum_j \kappa_j\right)$$

At electrophoretic steady state, $i_m = 0$, and equation 12 becomes:

$$E = \sum_j i_j / \sum_j \kappa_j = \frac{i_{ss}}{\sum_j \kappa_j} = \frac{I_{ss}}{A \sum_j \kappa_j} \quad (13)$$

where the subscript ss refers to the quantity measured at electrophoretic steady state, I is the current, and A is the cross-sectional area of the macro-ion interrogation chamber 61a (in cm²) measured in the plane normal to the ionic flows. Thus, the directed electrical field 114 can be determined from the conductivity of the solvent and the current at electrophoretic steady state. The solvent conductivity is measured by established procedures in a precision conductivity meter; the current is set at a predetermined value before the macro-ion analysis and maintained at that value throughout the analysis by the electrical power source supplying the current, as exemplified by electrical power source 96 of instrument complex 129. The perturbations in solvent composition within the macro-ion 112 concentration gradient which are required to maintain electroneutrality and the retarding effect of the macro-ions 112 at electrophoretic steady state on the flow of the solvent ions are considered to be experimentally insignificant when macro-ion-to-solvent ion charge-concentration ratios are below 0.02; values of this ratio in electrophoresis steady-state analyses are typically well below this limit.

Equation 11 may be integrated within appropriate limits to yield an expression relating the macro-ion 112 concentration at any point in the macro-ion 112 concentration gradient to some reference concentration within the macro-ion 112 concentration gradient. With the concentration of the macro-ions 112 at the upper surface of the semipermeable membrane 66 chosen as the reference concentration, integration of equation 11 yields:

$$\int_{c_{ms}}^{c_m} \frac{(1 + B'Fz'_m c_m) dc_m}{c_m} = \int_{x_s}^{x} \phi^{-1} Fz'_m dx \quad (14a)$$

$$c_m = c_{ms} \exp[\phi^{-1} Fz'_m(x_s - x) - B'Fz'_m(c_{ms} - c_m)] \quad (14b)$$

where x is any point along the x-axis in the macro-ion 112 gradient at concentration $c_m$, and the subscript s refers to the position of the semipermeable membrane 66 surface on the x-axis.

When polydisperse macro-ion systems (including reversibly associating macro-ion systems) are brought to electrophoretic steady state in the instrument 1, each of the different macro-ion species present forms a stable concentration gradient. These concentration gradients combine additively to form the observed concentration gradient stabilized at electrophoresis steady state:

$$\sum_i c_i = c = c_s \sum_i \exp[\phi^{-1} Fz'_i(x_s - x) - B'Fz'_i(c_{is} - c_i)] \quad (15)$$

where i indexes the macro-ion species. Equations 14a, 14b, and 15 (like equation 11) have their formal counterparts in the prior theory of equilibrium ultracentrifugation.

Following the mathematical treatment developed in equilibrium ultracentrifugation theory (see, for instance, Fujita, H. (1962), *Mathematical Theory of Sedimentation Analysis,* New York, N.Y., Academic Press), equation 15 and the definitions of the number-, weight-, and z-average moments can be combined to yield expressions measuring these moments of apparent molar diminished charge for polydisperse macro-ion systems:

$$\phi_c / \int_{c_a}^{c_a} \frac{dc}{d(\ln c)/dx} = \frac{Fz'_n}{(1 + B'Fz'_n c + \ldots)} = Fz'_{n,app} \quad (16)$$

$$\phi \left(\frac{d(\ln c)}{dx}\right) = \frac{Fz'_w}{(1 + 2B'Fz'_w c + \ldots)} = Fz'_{w,app} \quad (17)$$

$$\phi \left(\frac{d^2c/dx^2}{dc/dx}\right) = \frac{Fz'_z}{(1 + 2B'Fz'_w c + \ldots)^2} = Fz'_{z,app} \quad (18)$$

A single value of B' is permitted in these expressions if it can be assumed that the contribution to the nonideality by any macro-ion species present in the system undergoing electrophoretic steady-state analysis is proportional to the molar diminished charge of the species (i.e., $\ln y_i = (Fz'_i/Fz'_1)\ln y_1$. The integral in equation 16 is evaluated between c, the total concentration of the macro-ions at any point x along the x-axis in the macro-ion concentration gradient, and $c_a$, the concentration of the macro-ions at a point along the x-axis where the total macro-ion concentration is essentially zero. Thus, the number-average moment can be obtained only from those macro-ion concentration gradients stabilized at electrophoretic steady state which possess an experimentally accessible region where the macro-ion concentration approaches infinite dilution. However, like their counterparts in the prior theory of equilibrium ultracentrifugation, equations 16-18 allow measurements to be made at as many macro-ion concentration values throughout macro-ion concentration gradients maintained at electrophoretic steady state as is deemed appropriate for the particular requirements of a macro-ion analysis. It will be noted that equation 17 which measures the apparent weight-average molar diminished charge is identical in form to equation 11.

Equations 16-18 may also be applied to monodisperse macro-ions brought to electrophoretic steady state (e.g., the macro-ions 112). If the macro-ions examined at electrophoretic steady state behave ideally, a single value for the apparent molar diminished-charge moments will be determined by equations 16-18 at every point in the concentration gradient of the macro-ions; if the macro-ions behave nonideally, values of the apparent molar diminished-charge moments determined by equation 16-18 will be different at finite concentrations of the macro-ion due to the differing concentration dependencies of the number-, weight-, and z-average moments generated by the nonideality of the system.

Apparent molar diminished-charge moments may be divided by the constant $\phi$ to yield the corresponding reduced apparent molar diminished-charge moments which are analogous to effective reduced apparent molecular-weight moments encountered in the prior theory of equilibrium ultracentrifugation (see Introduction). Either apparent molar diminished-charge moments or reduced apparent molar diminished-charge moments may be used to determine assembly stoichiometries and association constants of reversibly associating macro-ion systems. Although analyses of such macromolecular systems by prior chemical-/quasi-chemical techniques, including equilibrium ultracentrifugation, often utilize absolute molecular-weight values, absolute molecular weights are not required in these calculations because assembly stoichiometries and association constants of reversibly associating systems reflect stoichiometric and concentration relationships among the species present in these systems and are not directly dependent on the molecular weights of the species involved. Accordingly, effective reduced apparent molecular-weight moments rather than absolute apparent molecular-weight moments are frequently utilized in the characterization of reversibly associating macromolecular systems by the prior technique of equilibrium ultracentrifugation.

To obtain accurate characterizations of reversibly associating macro-ion systems by electrophoretic steady-state analyses, it is necessary that at least the relative values of the molar diminished charges of the species present in the systems be known, either on the basis of reasonable estimation or from direct experimental determination. For reversibly mixed-associating systems, the required molar diminished-charge values can be obtained from electrophoretic steady-state analyses carried out with the isolated monomeric reactants; the molar diminished charges of the reactants in many instances can be assumed to be additive in estimating the molar diminished charges of larger, associated species in the systems. For many self-associating macro-ion systems, the molar diminished charge of the monomeric species need not be independently measured because the molar diminished charges of the assembled species can be assumed to be corresponding multiples of the molar diminished charge of the monomeric species.

Similarly, because weight-average-to-number-average molecular-weight ratios or other polydispersity parameters of mixtures of homologous macro-ions reflect relative concentrations of the species present, these parameters also may be determined by electrophoretic steady-state analyses. It is only necessary that the molar diminished charges of the species present in such systems be convertible to the corresponding molecular weights by a common factor; for a linear, charge-bearing and substantially free draining polymer system such as DNA, it is reasonable to assume that such a common factor applies and that, therefore, the weight-average-to-number-average molecular-weight ratio of the system is substantially equal to the weight-average-to-number-average molar diminished-charge ratio of the system.

Analyses of the concentration gradients of complex macro-ion systems brought to electrophoretic steady-state in the present invention are made following established mathematical procedures currently used to analyze data of such systems generated by the prior technique of equilibrium ultracentrifugation (procedures for analyzing reversibly associating systems by the prior technique of equilibrium ultracentrifugation including some which make use of effective reduced apparent molecularweight moments are discussed by several authors in *Advances in Ultracentrifugal Analysis,* Yphantis, D. A., Ed. (1969), Ann. N.Y., Acad. Sci., 164, Art. 1, Part VI). Although the apparent molar diminished-charge equations (equations 16–18) may be used in these analyses, the preferred approach in most studies would be to trial-fit the macro-ion concentration gradients of model systems generated by equation 15 to the experimental concentration gradients established at electrophoretic steady state. Where necessary, the apparent molar diminished charges of the macro-ionic species may be treated as adjustable parameters within suitable (usually narrow) limits. The best model fits to the experimental macro-ion concentration gradients would define the stoichiometries of assembly and the association constants in the case of reversibly associating macro-ion systems and the polydispersity parameters in the case of mixtures of homologous macro-ions.

The preceding mathematical description of the hypothetical macro-ion analysis with macro-ions 112 assumed no bulk solvent flow through the semipermeable membrane 66 during and after the formation of the macro-ion 112 concentration gradient. However, the presence of the macro-ions 112 at the upper surface of the semipermeable membrane 66 generates an osmotic pressure which reaches its maximum when the macro-ions 112 achieve electrophoretic steady state. The osmotic pressure promotes a flow of solvent (however negligible; see below) across the semipermeable membrane 66. If sufficient time is allowed, the flow will continue until the hydrostatic pressure difference as reflected by the levels of the solvent menisci 106$a$ and 106$b$ in the respective gas towers 24$a$ and 24$b$ equals the osmotic pressure; the osmotic pressure may be large enough as to require the fitting of the extension tube 30 to the instrument 1, as described above, to permit the establishment of the counterbalancing hydrostatic pressure.

If the bulk solvent flow rate across the semipermeable membrane(s), as represented by semipermeable membrane 66, fitted to the instrument 1 is excessive, it can significantly disrupt and distort the macro-ion concentration gradients established at electrophoretic steady state; disruption of the macro-ion gradients is most pronounced at the surfaces of the semipermeable membranes, as represented by the surface of semipermeable membrane 66, against which the macro-ion concentration gradients are formed. If the instrument 1 is fitted with semipermeable membranes, as exemplified by semipermeable membrane 66, fabricated from a material which exhibits significant bulk solvent flow at the mild pressure levels generated in the instrument 1 during electrophoretic steady-state analyses, which material may, nevertheless, possess other properties required for a particular electrophoretic steady-state analysis, the expected osmotic pressure at electrophoretic steady state must be neutralized. The osmotic pressure is neutralized by setting the solvent menisci 106$a$ and 106$b$ at levels at the beginning of the analysis which will create a hydrostatic pressure differential equal and counter to the expected osmotic pressure generated at electrophoretic steady state. Sometimes a preliminary electrophoretic steady-state analysis of the macro-ions to be examined at electrophoretic steady state may be necessary to determine the approximate range of the hydrostatic pressure required to counter the osmotic pressure generated. If very large hydrostatic pressure differentials are required, the extension tube 30 is fitted to the instrument 1, as described above. The gas-tower calibration lines 26 and the extension-tube calibration lines 34 are used to conveniently establish the required difference in the levels of the solvent menisci 106$a$ and 106$b$.

Bulk solvent flow through semipermeable membranes fabricated of cellulosic film (e.g., Spectra/Por 1), however, is very small under pressures comparable to the osmotic pressures generated in the instrument 1 during electrophoretic steady-state analyses. Accordingly, when the semipermeable membranes, as exemplified by semipermeable membrane 66, fitted to the instrument 1 are fabricated of cellulosic film, the effect of bulk solvent flow through said membranes, as exemplified by semipermeable membrane 66, on the integrity of macro-ion concentration gradients established at electrophoretic steady state in the instrument 1 is substantially negligible, even when the osmotic pressures generated at electrophoretic steady state are not neutralized by a counter hydrostatic pressure. Therefore, when semipermeable membranes, as represented by semipermeable membrane 66, fabricated of cellulosic film are employed in the instrument 1, the solvent menisci 106a and 106b can be conveniently set at the beginning of a macro-ion analysis to the approximate midpoints of the respective gas towers 24a and 24b.

The time required after the electrical potential difference is first applied to the electrodes 35a and 35b for the macro-ion samples in the instrument 1 to achieve electrophoretic steady state during a macro-ion analysis is dependent on several factors. In general, the time required for macro-ions to attain electrophoretic steady state is inversely proportional to the diffusion coefficient of the macro-ions. Accordingly, large macro-ions typically take longer to achieve electrophoretic steady state than smaller macro-ions.

A particularly sensitive parameter affecting the time required for macro-ion samples to achieve electrophoretic steady state in the instrument 1 is the length of the volume occupied by each macro-ion sample at the outset of the analysis along the x-axis as measured from the semipermeable membrane surface, as exemplified by the surface of semipermeable membrane 66,. For a constant directed electrical field, the time required for macro-ion samples to attain electrophoretic steady state in the instrument 1 can be expected to vary with the square of this distance (this same dependence is encountered in the time required for macromolecular samples to reach sedimentation equilibrium in the analytical ultracentrifuge). Therefore, in order that electrophoretic steady state be achieved in a tractable period of time after a potential difference is applied across the electrodes 35a and 35b —within 8-36 hours—it is necessary that each macro-ion sample introduced into the instrument 1 be localized at the semipermeable membrane, as exemplified by semipermeable membrane 66, at the beginning of the macro-ion analysis, typically occupying a volume which extends no more than 3-4 mm away from the surface of the membrane, as exemplified by the surface of semipermeable membrane 66. Accordingly, when the instrument 1 is fitted with a single semipermeable membrane, as exemplified by semipermeable membrane 66 fitted to cell-block-component embodiment 99, the macro-ion sample introduced into the instrument following the relevant procedure described earlier normally extends no more than approximately 4 mm from the semipermeable membrane surface, as exemplified by the surface of semipermeable membrane 66.

The distance between semipermeable membranes fitted above and below the short (vertical dimension) interrogation cells, as exemplified by semipermeable membranes 66 fitted to upper interrogation cell 58' in cell-block-component embodiment 101, is approximately 4 mm. Accordingly, macro-ion samples loaded into interrogation cells fitted with two semipermeable membranes, as exemplified by upper interrogation cell 58' fitted with semipermeable membranes 66, by the relevant procedure described earlier typically attain electrophoretic steady state within the 8-36-hour time frame discussed above.

Macro-ion concentration gradients established at electrophoretic steady state in the instrument 1 also typically extend no more than 4 mm—and often less than 3 mm—from the semipermeable membrane surfaces, as exemplified by the surface of semipermeable membane 66, against which said gradients are formed. However, some complex macro-ion systems, as for example selected reversibly associating macro-ion systems which exhibit pronounced nonideal behavior, are often preferably analyzed at electrophoretic steady state when the macro-ions of such systems are established in concentration gradients which exceed the aforesaid limits. Such longer macro-ion concentration gradients are conveniently established at electrophoretic steady state in taller interrogation cells, as exemplified by interrogation cell 87 of cell-block-component embodiment 100. Macro-ion concentration gradients extending more than 4 mm in length at electrophoretic steady state are established within time frames which typically exceed the 8-36-hour duration needed for the shorter macro-ion concentration gradients discussed above.

Whenever it is experimentally feasible, macro-ion concentration gradients are established at electrophoretic steady state in the instrument 1 with dimensional specifications which are particularly tractable to precise measurement and analysis. For example, the specifications of macromolecular concentration gradients encountered in the prior technique of equilibrium ultracentrifugation which have been found to facilitate precise measurement by Rayleigh interference optical systems would generally apply to macro-ion concentration gradients similarly measured in the preferred embodiment 1. Thus, macro-ion concentration gradients which are established at electrophoretic steady state in the longer optical-path interrogation cells (approximately 20 mm), as exemplified by interrogation cell 58, and approach infinite dilution within 4 mm of the semipermeable membrane against which they are formed, as represented by semipermeable membrane 66, should generate absolute values for the quantity, $d(\ln c_m)/dx$ (equation 11) between the approximate limits of 10 $cm^{-1}$ and 40 $cm^{-1}$ at all values of x when the macro-ion concentration gradients are interrogated by Rayleigh interference optical systems, as represented by Rayleigh interference optical system 115. Because the optimal range for the absolute value of the quantity $d(\ln c_m)/dx$ is related inversely to the optical path of the interrogation cells, as represented by interrogation cell 58, within which macro-ions achieve electrophoretic steady state, optimal absolute values for $d(\ln c_m)/dx$ are higher when the shorter optical-path interrogation cells (approximately 4 mm), as exemplified by interrogation cell 87, are fitted to the instrument 1 than when the longer optical-path interrogation cells, as exemplified by interrogation cell 58, are fitted to the instrument 1. Typically, macro-ion concentration gradients maintained at electrophoretic steady state in longer optical-path interrogation cells, as exemplified by interrogation cell 58, fitted to the instrument 1 exhibit concentrations of macro-ions of between 1 and 4 grams/liter at the semipermeable membrane surfaces, as exemplified by the surface of semipermeable membrane 66, against which the macro-ion concentration gradients are formed.

The applied directed electrical field which in conjunction with the force of diffusion is required to maintain macro-ion concentration gradients with the desired dimensional specifications at electrophoretic steady state in the instrument 1 is determined from an evaluation of several factors: the estimated or measured value(s) of the molar diminished charge(s) of the macro-ionic species undergoing electrophoretic steady-state analysis, the temperature of the analysis, the desired range for the values of the quantity $d(\ln c)/dx$ (equation 11), and the optical path of the interrogation cell(s), as represented by interrogation cell 58, fitted to the instrument 1. The electrical current which will establish the desired directed electrical field is calculated from the measured conductivity of the solvent, the strength of the directed electrical field, and the cross-sectional area of the macro-ion interrogation chamber(s) in the horizontal plane (equation 12), as exemplified by interrogation chamber 61a of interrogation cell 58, fitted to the instrument 1; typical current levels fall within 0.05–1.0 milliamperes. The current level in the instrument 1 is maintained at the desired value throughout the macro-ion and solvent analyses by an electrical power source with the specifications discussed earlier, as exemplified by electrical power source 96 of instrument complex 129. Current regulatory circuitry is a preferred component of the electrical power source, as represented by electrical power source 96, because the electrical resistance of the instrument 1 during the course of a macro-ion or solvent analysis can change, albeit by only 1–2% with typical solvent systems.

In addition to the criteria discussed earlier for selecting the type and number of interrogation cells to be fitted to the instrument 1 in preparation for an electrophoretic steady-state analysis, other considerations may be important. Multi-cell operation in the instrument 1, as exemplified by the use of the cell-block-component embodiment 101 in the instrument I, allows several electrophoretic steady-state analyses to be carried out simultaneously; however, such analyses are restricted to a common temperature, directed electrical field, and solvent. For some electrophoretic steady-state studies, these restrictions are acceptable and often convenient, but for others they are not.

Single-semipermeable membrane operation in the instrument 1, as exemplified by the use of the cell-block-component 99 in the instrument 1, has the advantage over its multiple-semipermeable membrane alternative, as exemplified by the use of the cell-block-component embodiment 101 in the instrument 1, of permitting sequential macro-ion analyses to be carried out with a different macro-ion sample in each of the analyses without the need of disassembling and reassembling the instrument 1 between analyses. This operational simplification can greatly reduce the turnaroud between macro-ion analyses. Moreover, both the directed electrical field and the temperature (but not the solvent) can be changed for each of the analyses. Macro-ion samples can be easily removed after each macro-ion analysis with the syringe 107 and needle 108 by the procedure described earlier for removing macro-ion samples in preparation for making solvent analyses when the instrument 1 is fitted for single-semipermeable membrane operation, as represented by the instrument 1 fitted with the cell-block-component embodiment 99. After a macro-ion sample has been removed from the instrument 1 following an macro-ion analysis, a new macro-ion sample may be introduced immediately, and only one solvent analysis is required for all of the macro-ion analyses carried out within a series of such analyses. Occasionally, it is necessary to charge the instrument 1 with new solvent during a series of macro-ion analyses as just described when it is suspected that a significant fraction of the solvent has undergone chemical decomposition at the electrodes, as exemplified by electrode 35a.

The employment of interrogation cells in the instrument 1 with semipermeable membranes positioned both above and below the interrogation cells, as represented by upper interrogation cell 58' and semipermeable membranes 66 of cell-block-embodiment 101, permits the formation of partial or "truncated" macro-ion concentration gradients at electrophoretic steady state in the instrument 1, i.e., macro-ion concentration gradients which exhibit finite macro-ion concentrations at all values of x between the semipermeable membrane surfaces, as represented by the surfaces of semipermeable membranes 66 fitted to cell-block-component embodiment 101. "Truncated" macro-ion concentration gradients stabilized at electrophoretic steady state in the instrument 1 are useful in the study of reversible macro-ion associations at high macro-ion concentrations and, typically, are tractable to optical analysis at lower absolute values of the quantity $d(\ln c_m)/dx$ than are optimal for macro-ion concentration gradients, stabilized at electrophoretic steady state, which extend to infinite dilution within the interrogation cell, as represented by interrogation cell 58, fitted to the instrument 1. However in most cases, "truncated" macro-ion concentration gradients established in the short (vertical dimension) interrogation cells fitted to the instrument 1 can be expected to achieve electrophoretic steady state within the 8-36-hour time frame normally required for macro-ion gradients which extend to infinite dilution within said interrogation cells, as exemplified by upper interrogation cell 58'. "Truncated" macro-ion concentration gradients at electrophoretic steady state can also be formed in the interrogation cell 58 of the cell-block-component embodiment 99 if the cell gasket 64 is replaced with a semipermeable membrane 66. In the analysis of selected macro-ionic systems, it is preferable to generate "truncated" concentration gradients stabilized at electrophoretic steady state which extend longer than 4 mm, in which case taller interrogation cells, as represented by interrogation cell 87 of cell-block-component embodiment 100, are utilized in the instrument 1. As discussed above, such longer macro-ion concentration gradients are typically established at electrophoretic steady state within time frames beyond the 8-36-hour time frame usually required for shorter concentration gradients.

It should be noted that number-average moments (equations 16) can not be determined from "truncated" macro-ion concentration gradients stabilized at electrophoretic steady state because these gradients do not extend to infinite dilution. Moreover, when a Rayleigh interference optical system, as exemplified by Rayleigh interference optical system 115 of instrument complex 129, is employed to record "truncated" macro-ion concentration gradients at electrophoretic steady state in the instrument 1, it is necessary to establish relative macro-ion concentrations within these gradients by invoking the principle of conservation of macro-ion mass or by applying other procedures similar to those used in analyzing concentration gradients encountered in the prior art of equilibrium ultracentrifugation; such procedures are generally not required when single- or dual-beam absorption optical systems are employed to record "truncated" macro-ion concentration gradients at electrophoretic steady state in the instrument 1.

Density inversions within macro-ion concentration gradients established at electrophoretic steady state are potentially disruptive of the gradients; gravity-induced dissipations of the inversions can lead to intermittent mass flows within the macro-ion concentration gradients, despite the stabilizing influences of diffusion and the imposed directed electrical field. These gravitational effects are minimized when macro-ion concentration gradients established at electrophoretic steady state possess downward directed, positive, density gradients. Solutions of the vast majority of macro-ionic species dialyzed against typical, low-salt, aqueous solvents form vectorially coincident density and concentration gradients. These macro-ion solutions form stable concentration gradients established at electrophoretic steady state against the upper surfaces of semipermeable membranes fitted to the instrument 1, as represented by the upper surface of semipermeable membrane 66 located below interrogation cell 58 of cell-block-component embodiment 99 (FIGS. 3a, 11a and 11b). However, solutions of selected macro-ionic species (e.g., selected aqueous solutions of some lipoproteins) form vectorially opposed density and concentration gradients. Accordingly, such macro-ion solutions form stable concentration gradients established at electrophoretic steady state against the lower surfaces of semipermeable membranes fitted to the instrument 1, as exemplified by the lower surface of semipermeable membrane 92 located above interrogation cell 87 of cell-block-component embodiment 100.

For single-semipermeable membrane operation in the instrument 1, as exemplified by the operation of the instrument 1 fitted with the cell-block-component embodiment 99, with macro-ion solutions exhibiting vectorially opposed concentration and density gradients, the single semipermeable membrane is placed above the interrogation cell and the cell gasket is placed below the interrogation cell during assembly of the cell-block-component embodiment, as represented by semipermeable membrane 66, interrogation cell 58, and cell gasket 64 fitted to cell-block-compound embodiment 99. Prior to charging the instrument 1 with solvent, the upper sample-loading-port stopper 47a and the lower sample-loading-port stopper 47b are interchanged between the respective upper and lower sample-loading-port fittings 43a and 43b. These modifications allow a macro-ion sample to be introduced through the lower sample-loading port 41b and deposited at a point just below the semipermeable membrane, as represented by semipermeable membrane 66 fitted as described above to cell-block-component embodiment 99. The macro-ion solution is introduced into the instrument 1 with the syringe 107 and needle 108 following the procedure described earlier for loading a macro-ion sample into the instrument 1 in preparation for single-semipermeable-membrane operation except that the instrument 1 is physically lifted to allow the needle 108 to be inserted through the self-sealing valve 49 located in the upper sample-loading-port stopper 47a. It has been found that subsequent (careful) handling oithe instrument 1 fitted with the cell-block-component embodiment 99 or with the cell-block-component embodiment 99 modified as described above, after a macro-ion sample has been loaded, does not promote intermixing between the solvent and the macro-ion sample.

The electrical current flow required to support the directed electrical field in the instrument 1 during electrophoretic steady-state analyses causes chemical decomposition of solvent components at the interfaces between the solvent and the electrodes, as exemplified by electrode 35a. Some of the decomposition products so produced are gaseous, a portion of which is dissolved into the solvent and the remainder forms into gas bubbles which rise vertically in a thin stream from the electrodes, as represented by electrode 35a. The lengthy duration of the macro-ion analyses carried out in the preferred embodiment 1, sometimes 36 hours or even longer as discussed above, can result in the production of significant amounts of the aforesaid gaseous products; the amount of such gaseous products produced during an electrophoretic steady-state analysis depends on the composition of the solvent, the wattage required to support the directed electrical field, and the duration of the analysis.

The design of the preferred embodiment 1 allows undissolved gaseous decomposition products formed at the electrodes 35a and 35b during electrophoretic steady-state analyses to rise as bubbles into the respective gas towers 24a and 24b. After breaking through the solvent menisci 106a and I06b located in the respective gas towers 24a and 24b (or one gas tower, as represented by gas tower 24a, and the extension tube 30, if utilized as described earlier), the gas bubbles are vented through the gas-venting tubes 109 to the outside of the instrument complex, as represented by instrument complex 129. The gas-venting tubes 109 are desirable because some gaseous decomposition products formed at the electrodes 35a and 35b during electrophoretic steady-state analyses in the instrument 1 are potentially corrosive and could possibly damage the optical system(s) fitted to the instrument complex, as represented by Rayleigh interference optical system 115 fitted to instrument complex 129.

Several design features of the preferred embodiment 1 facilitate the establishment of well-defined macro-ion concentration gradients stabilized at electrophoretic steady state which can be accurately described by the equations of electrophoretic steady-state theory summarized earlier: Because the electrodes 35a and 35b are disposed parallel to the direction of the ionic flows in the instrument 1 when directed electrical fields are established in the instrument 1 (FIG. 3a), the electrodes 35a and 35b are, in effect, similar to point sources of electrical potential with regard to the geometry of the directed electrical fields. Consequently, any changes in the resistance at the solvent-electrode interfaces, as exemplified by the interface between the solvent and electrode 35a, along the lengths of the electrodes 35a and 35b during the course of an electrophoretic steady-state analysis do not significantly alter the geometry of the directed electrical field. Although the electrodes 35a and 35b are similar to point sources, they are sufficiently far (via the ionic flow path; see above) from the interrogation cell(s) fitted to the instrument 1, as represented by interrogation cell 58 of cell-block-component embodiment 99, to ensure that the directed electrical fields established in the instrument 1 during electrophoretic steady-state analyses vary by a negligible amount between the center of a macro-ion interrogation chamber of an interrogation cell and any point near a cell window, as represented by interrogation chamber 61a and either cell window 59 of interrogation cell 58 fitted to oell-block-component embodiment 99. Moreover, the upper and lower partition slots 22a and 22b are laterally positioned to ensure that substantially uniform directed electrical fields are established across the lateral axis of the macro-ion interrogation chambers of interrogation cells fitted to the instrument 1, as represented by interrogation chamber 61a of interrogation cell 58 fitted to cell-block-component embodiment 99, during electrophoretic steady-state analyses.

The upper partition slot 22a and the upper partition 18a in effect extend the rectangular hole 82a located in the upper cell-block assembly 74a through the upper inner chamber 20a to the upper partition slot 22a; and, similarly, the lower partition slot 22b and the lower partition 18b in effect extend the rectangular hole 82b located in the lower cell-block assembly 74b through the lower inner chamber 20b to the lower partition slot 22b. This extension, in effect, of the rectangular holes 82a and 82b is a principal design element contributing to the uniformity of the directed electrical fields established in the macro-ion interrogation chambers of the interrogation cells fitted to the instrument 1, as exemplified by interrogation chamber 61a of interrogation cell 58 fitted to cell-block-component embodiment 99; an actual, physical, extension of rectangular holes 82a and 82b to the respective upper and lower partition slots 22a and 22b as an alternative design to the present preferred embodiment 1 was less preferred because the alternative design would exacerbate both the problem of air bubble removal during the solvent-charging procedure and the problem of cleaning the upper and lower instrument assemblies 2a and 2b, if required, between electrophoretic steady-state analyses.

The macro-ion interrogation chambers of each cell-block-component embodiment, as represented by interrogation chamber 61a of interrogation cell 58 fitted to cell-block-component embodiment 99, and the rectangular holes in the cell-support pieces and in the cell gasket (if present), as represented by rectangular holes 68a and 68b of respective upper and lower cell-support pieces 67a and 67b, rectangular hole 65 of cell gasket 64, possess identical corresponding dimensions in the horizontal plane and are aligned coextensively when each cell-block-component embodiment, as represented by cell-block-component embodiment 99, is fitted to the instrument 1. The aforesaid holes and interrogation chambers present in each cell-block-component embodiment, as represented by holes 65, 68a, and 68b and interrogation chamber 61a present in cell-block-component embodiment 99, together form a vertically disposed, rectangular hole with parallel walls which is interrupted by the horizontally disposed surfaces of the semipermeable membranes fitted to the cell-block-component embodiment, as represented by semipermeable membrane 66 fitted to cell-block-component embodiment 99. The aforesaid design features of the preferred embodiment 1 ensure that the directed electrical fields established within the instrument 1 during electrophoretic steady-state analyses are (1) substantially linear within the macro-ion interrogation chamber(s) of the interrogation cell(s), as exemplified by interrogation chamber 61a of interrogation cell 58, fitted to the instrument I; and (2) substantially perpendicular to, and substantially uniform over, the surfaces of the semipermeable membrane(s), as represented by the surfaces of semipermeable membrane 66, fitted to the instrument 1.

Consequently, the directed electrical fields within the instrument 1 support ionic flows (macro-ions and solvent ions) during electrophoretic steady-state analyses which are also (1) substantially linear within the macroion interrogation chamber(s) of the interrogation cell(s), as exemplified by interrogation chamber 61a of interrogation cell 58, fitted to the preferred embodiment 1; and (2) substantially perpendicular to, and substantially uniform over, the surfaces of the semipermeable membrane(s), as exemplified by the surfaces of semipermeable membrane 66, fitted to the instrument 1. The vectors of the macro-ion concentration gradients established at electrophoretic steady state within the instrument 1 are, therefore, unidimensional and disposed substantially perpendicular to the horizontal surfaces of the semipermeable membranes, as exemplified by the surfaces of semipermeable membrane 66, against which said gradients are formed. Moreover, each macro-ion concentration gradient established at electrophoretic steady state within the instrument 1 is substantially uniform over the entire surface of the semipermeable membrane, as exemplified by the upper surface of semipermeable membrane 66 of cell-block-component embodiment 99, against which the said gradient is formed; more specifically, when macro-ion samples are established at electrophoretic steady state in the instrument 1, any horizontally disposed lamella within a macro-ion interrogation chamber, as represented by interrogation chamber 61a, fitted to the instrument 1 is of uniform chemical composition throughout the lamella to within experimentally negligible limits. Thus, the macro-ion concentration gradients established and maintained at electrophoretic steady state within the preferred embodiment 1 can be described with substantial accuracy by the relevant equations of electrophoretic steady-state theory presented above.

Macro-ion concentration gradients maintained at electrophoretic steady state within the preferred embodiment 1 can be quantitatively interrogated by several types of optical systems capable of measuring the concentrations of macro-ions dissolved in aqueous and other polar solvents. Included among such optical systems are single-and dual-beam absorption optical systems (not shown) and Rayleigh interference optical systems, as represented by Rayleigh interference optical system 115 fitted to instrument complex 129. Double-chamber interrogation cells, as exemplified by interrogation cell 58 of cell-block-component embodiment 99, fitted to the instrument 1 are appropriately interrogated by selected dual-beam optical systems including dual-beam absorption optical systems (not shown) and Rayleigh interference optical systems, as represented by Rayleigh interference optical system 115. Single-chamber interrogation cells, as exemplified by interrogation cell 87 fitted to cell-block-component embodiment 100, fitted to the instrument 1 are appropriately interrogated by either selected single-beam optical systems, as exemplified by a single-beam absorption optical system (not shown) or selected dual-beam optical systems, as for example a Rayleigh interference optical system, as represented by Rayleigh interference optical system 115.

During electrophoretic steady-state analyses, the preferred embodiment 1 is placed on a precision mount (not shown), as described earlier, which aligns the instrument 1 in the beam(s) of optical energy of an appropriate optical system, as exemplified by Rayleigh interference optical system 115. When the instrument 1 is aligned in an appropriate single-beam optical system, the beam of optical energy of the optical system is aligned along the axis 113a and interrogates the macro-ion interrogation chamber(s), as represented by interrogation chamber 90 of interrogation cell 87 fitted to cell-block-component embodiment 100, present in the instrument 1. When the instrument 1 is aligned in an appropriate dual-beam optical system, one beam of optical energy of the optical system is aligned along the axis 113a and interrogates the macro-ion interrogation chamber(s), as represented by interrogation chamber 61a of interrogation cell 58 fitted to cell-block-component embodiment 99, present in the instrument 1; the other beam of optical energy of the dual-beam optical system is aligned along the axis 113b and interrogates the reference interrogation chamber(s), as exemplified by interrogation chamber 61b of interrogation cell 58, present in the instrument 1. The axes 113a and 113b are substantially parallel and disposed substantially normal to the cell windows of the interrogation cell(s), as represented by cell windows 59 of interrogation cell 58, fitted to the cell block 3 when the instrument 1 is aligned in an appropriate optical system.

When the instrument 1 is aligned in an appropriate optical system and is fitted with a single interrogation cell, as exemplified by interrogation cell 87 of cell-block-component embodiment 100, the axis 113a intersects the center of the macro-ion interrogation chamber of the interrogation cell, as exemplified by interrogation chamber 90 of interrogation cell 87. When the instrument 1 is aligned in an appropriate optical system and is fitted with several interrogation cells, as exemplified by upper, middle, and lower interrogation cells 58', 58", and 58"' of cell-block-component embodiment 101, the axis 113a intersects the midpoint of the line which connects the centers of the macro-ion interrogation chambers of the upper- and the lower-most of the interrogation cells, as represented by interrogation chambers 61a' and 61a"' of respective upper and lower interrogation cells 58' and 58"'.

When the instrument 1 is aligned in an appropriate optical system and is fitted with a single double-chamber interrogation cell, as represented by interrogation cell 58 of cell-block-component embodiment 99, the axis 113b intersects the center of the reference interrogation chamber of the interrogation cell, as exemplified by interrogation chamber 61b of interrogation cell 58. When the instrument 1 is aligned in an appropriate optical system and is fitted with several double-chamber interrogation cells, as represented by upper, middle, and lower interrogation cells 58', 58", and 58"', of cell-block-component 101, the axis 113b intersects the midpoint of the line which connects the centers of the upper- and the lower-most of the reference interrogation chambers of the interrogation cells, as represented by interrogation chambers 61b' and 61b"' of upper and lower interrogation cells 58' and 58"', respectively.

When the instrument 1 is aligned in an appropriate optical system and is fitted with single-chamber interrogation cell(s), as represented by interrogation cell 87 of cell-block-component embodiment 100, the axis 113b passes through the reference-beam channel, as represented by reference-beam channel 132 of lower cell-support piece 93b, and does not intersect any physical element of the instrument 1. However, if the instrument 1 is fitted with single-chamber interrogation cell(s), as represented by interrogation cell 87, and is aligned in a Rayleigh interference optical system, as exemplified by Rayleigh interference optical system 115, the beam of optical energy of the said optical system aligned along the axis 113b passes through an adjustable optical-path compensator, as represented by adjustable optical-path compensator 130 fitted to Rayleigh interference optical system 115. The adjustable optical-path compensator, as represented by adjustable optical-path compensator 130, mimics the optical properties of the reference interrogation chamber(s) of double-sector interrogation cell(s), as exemplified by interrogation chamber 61b of interrogation cell 58, fitted to the instrument 1 and thus functions as an optical surrogate for the reference interrogation chamber(s), as represented by interrogation chamber 61b. An adjustable optical-path compensator, as exemplified by adjustable optical-path compensator 130, is not a required optical element in a dual-beam absorption optical system employed to interrogate single-chamber interrogation cell(s), as represented by interrogation cell 87, fitted to the instrument 1.

The lateral dimensions of the interrogation cells fitted to instrument 1, as represented by interrogation cell 58 of cell-block-component embodiment 99, require that the beam(s) of optical energy of appropriate optical systems employed to interrogate macro-ions maintained at electrophoretic steady state in the preferred embodiment 1 be no more than approximately 1.5 mm in width and that the two substantially parallel beams of optical energy of appropriate dual-beam optical systems so employed be spaced approximately 5 mm apart at the point in the optical system where the beams of optical energy encounter the instrument 1. When the instrument 1 is aligned in an appropriate single- or dual-beam optical system, the beam of optical energy of the optical system aligned along the axis 113a possesses sufficient height to intersect both the upper-and lower-most membranous elements of the cell-blockcomponent embodiment fitted to the instrument 1, as represented by upper and lower semipermeable membranes 92 and 92' fitted to cell-block-component 100. Similarly, when the instrument 1 is aligned in an appropriate dualbeam optical system, the beam of optical energy from the dual-beam optical system aligned along the axis 113b possesses sufficient height to intersect both the upperand lower-most membranous elements of the cell-blockcomponent embodiment fitted to the instrument 1, as represented by semipermeable membrane 66 fitted above upper interrogation cell 58' and semipermeable membrane 66 fitted below lower interrogation cell 58"' of cell-block-component embodiment 101. Thus, when the instrument 1 is aligned in an appropriate optical system and is fitted with a cell-block-component embodiment featuring several interrogation cells disposed in vertical series, as represented by upper, middle, and lower interrogation cells 58', 58", and 58"' of cell-block-component embodiment 101, all of the interrogation cells, as exemplified by upper, middle, and lower interrogation cells 58 , 58", and 58"', are interrogated simultaneously by the beam(s) of optical energy of the optical system. Accordingly, the height of the beam(s) of optical energy is varied between the approximate limits of 4 mm and 12 mm, depending of the number and height of the interrogation cell(s), as represented by interrogation cell 58 of cell-block-component embodiment 99, fitted to the instrument 1.

When the preferred embodiment 1 is aligned in an appropriate optical system, as exemplified by Rayleigh interference optical system 115, and the macro-ion sample(s) present in the instrument 1 have achieved electrophoretic steady state, the several features of the preferred embodiment 1 described earlier and the dimensions and disposition of the beam(s) of optical energy of the optical system ensure that each light ray of the beam of optical energy aligned along the axis 113a which enters each macro-ion interrogation chamber, as exemplified by interrogation chamber 61a of interrogation cell 58, fitted to the instrument 1 encounters macro-ion solution of substantially constant concentration at every point between the cell windows, as represented by cell windows 59 of interrogation cell 58. The said optical system is thereby capable of registering a substantially precise and substantially quantitatively accurate optical record of each macro-ion concentration gradient maintained at electrophoretic steady state in the instrument 1. Moreover, the optical energy-beam dimensions discussed above are very similar to the dimensions of the beam(s) of optical energy produced by absorption and Rayleigh interference optical systems incorporated into many research instruments in current use, including the Beckman Model E Analytical Ultracentrifuge, for the purpose of interrogating solutions of macromolecules. Thus it is contemplated that any among several appropriate optical systems of established design can be adapted for incorporation into the instrument complex, as exemplified by instrument complex 129, for the purpose of interrogating macro-ion concentration gradients maintained at electrophoretic steady state in the preferred embodiment 1.

The schematic representations of solvent analysis and macro-ion analysis interferograms 102a and 102b (FIGS. 12a and 12b) illustrate optical records that could be expected from a typical electrophoretic steady-state analysis carried out in the preferred embodiment 1 fitted with the cell-block-component embodiment 99 and interrogated by a Rayleigh interference optical system, as represented by Rayleigh interference optical system 115 of instrument complex 129. The solvent analysis interferogram 102a and the macro-ion analysis interferogram 102b are each delimited at the top by optical artifact 103a caused by the cell gasket 64 and delimited at the bottom by optical artifact 103b caused by the semipermeable membrane 66. The interference fringes of the solvent analysis interferogram 102a are vertical throughout the interferogram 102a reflecting no relative changes, as expected, in the refractive indices of the solvent throughout the volumes of the interrogation chambers 61a and 61b between the cell gasket 64 and the semipermeable membrane 66. The curvature of the interference fringes of the macro-ion interferogram 102b near the optical artifact 103b record an increase in the refractive index of the macro-ion solution contained in the macro-ion interrogation chamber 61a near the semipermeable membrane 66 over the refractive index of the solvent contained in the solvent interrogation chamber 61b. The degree of displacement of the interference fringes at any point in interferogram 102b is substantially proportional, linearly, to the concentration of the macro-ions at the corresponding point in the macro-ion interrogation chamber 61a and is thus a measure of the macro-ion concentration gradient established at electrophoretic steady state. Interferograms similar to the solvent analysis and macro-ion analysis interferograms 102a and 102b are obtained when the instrument 1 is fitted with the cell-block-component embodiments 100 and 101; however, when the instrument 1 is fitted with the cell-block-component embodiment 101, the Rayleigh interference optical record consists of three interferograms disposed in vertical series for both the solvent analysis and the macro-ion analysis interferograms.

Figure 13A:
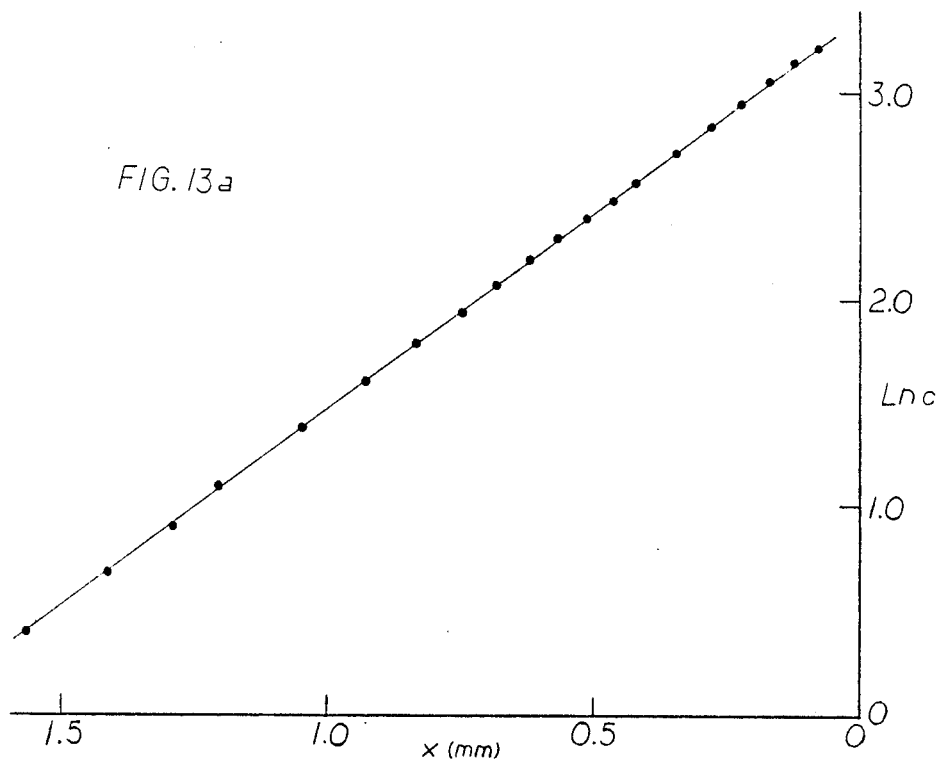
FIG. 13a is a graphic presentation of results from an electrophoretic steady-state analysis conducted in the preferred embodiment.
Figure 13B:
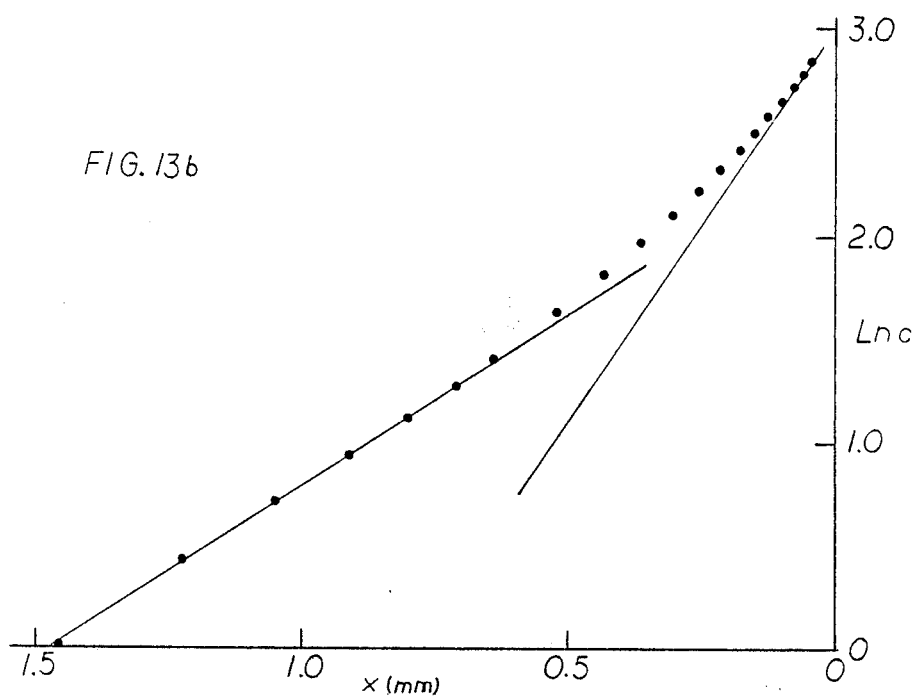
FIG. 13b is a graphic presentation of results from another electrophoretic steady-state analysis conducted in the preferred embodiment.

Graphic representations of data from two electrophoretic steady-state analyses carried out in the preferred embodiment 1 are depicted in FIGS. 13a and 13b. For both analyses, the instrument 1 was fitted with the cell-block-component embodiment 99 and the semipermeable membrane 66 was fabricated from cellulosic film (Spectra/Por 1). The optical records of the macro-ion and solvent analyses were made with a Rayleigh interference optical system similar in basic design to the Rayleigh interference optical system 115 of the instrument complex 129, except that the interference images were photographed. Digital records of the Rayleigh interferograms were determined manually on an optical micro-comparator. The data from both analyses are plotted as ln $c_m$ versus x. The slope of these plots at any point, $d(\ln c_m)/dx$, is proportional to the weight-average apparent molar diminished charge of the macro-ions under analysis at the point in the macro-ion gradient where the slope is determined (equation 11). Data plots of this type graphically illustrate the presence or absence of polydispersity and the presence or absence positive nonideal behavior in the macro-ion system examined: a monodisperse, ideal-behaving macro-ion sample produces a linear plot of ln $c_m$ versus x; an upward curving plot is strong evidence of the presence of polydispersity in the macro-ion sample; and downward curvature of the plot reveals positive nonideal behavior of the macro-ion sample.

FIG. 13a depicts a plot of ln c versus x derived from the interferogram of a solution of purified ovalbumin (Sigma, Grade VI; Sigma Chemical Co., St. Louis, MO) brought to electrophoretic steady state in the instrument 1 as described above. The protein was dissolved in an aqueous solvent containing 50 mM (millimoles/liter) KCl, 5 mM HEPES (N-2-hydroxyethyl piperazine-N'-2-ethane sulfonic acid), 0.5 mM EDTA (ethylenediamine tetraacetic acid), pH 7.6. The temperature of the electrophoretic steady-state analysis was 21° C. The ovalbumin concentration gradient at electrophoretic steady state extended to infinite dilution within 3 mm of the semipermeable membrane 66 surface, and the quantity $d(\ln c)/dx$ was measured to be $-21.3$ cm$^{-1}$ (the sign of the abscissa—and therefore of the macro-ion concentration gradient as well—is determined by the direction of the electrical field relative to the direction of the macro-ion gradient). The plot is substantially linear over a wide concentration range, as would be expected for this globular, monodisperse, ideal-behaving protein (from approximately 0.05 to 2.3 grams/liter). From equation 17, $Fz'_{w,app}$ was calculated to be $-1.12 \times 10^{15}$ esu/mole. Analyzed as a mixture of a homologous series of macro-ions, the number-average-to-weight-average molecular-weight ratio is approximately 1.0.

FIG. 13b is a plot of ln c versus x derived from the interferogram of a solution containing a mixture of the calf thymus histone (protein) complexes H2A-H2B dimer and H3-H4 tetramer (prepared by the inventor) brought to electrophoretic steady state in the instrument 1 as described above. The proteins were dissolved in an aqueous solvent containing 1M (moles/liter) KCl, 5 mM HEPES, 0.5 mM EDTA, pH 7.2, and the temperature of the electrophoretic steady-state analysis was 21° C. The concentration gradient of the histone mixture at electrophoretic steady state extended to infinite dilution within 4 mm of the semipermeable membrane 66 surface. The plot exhibits upward curvature indicative of an increasing value of the quantity $d(\ln c)/dx$ (i.e., polydispersity), and therefore of $Fz'_{w,app}$ as well, with macro-ion concentration. This result is consistent with published evidence (Godfrey, J. E., Eickbush, T. H., & Moudrianakis, E. N. (1980) Biochemistry 19, 1339) which suggest that the calf thymus histone system examined undergoes reversible association to form an octameric species, $(H2A-H2B-H3-H4)_2$, in high ionic-strength solvents according to the following assembly stoichiometry:

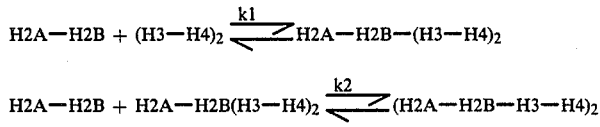

From equation 17, it was calculated that $Fz'_{w,app}$ increases from $8.6 \times 10^{14}$ esu/mole, at the low concentration end of the macro-ion gradient, to $1.90 \times 10^{15}$ esu/mole at the high concentration end of the macro-ion gradient (tangents drawn to the curve, FIG. 13b). These data can be closely fitted to the assembly stoichiometry depicted above with values for $k_1$ and $k_2$ of 4.1 liters/gram and 3.7 liters/gram, respectively.

Thus it will be appreciated from the above that as a result of the present invention, highly effective apparatuses and methods are provided by which the principal objective, among others, is completely fulfilled. It will be equally apparent and is contemplated that modification and/or changes may be made in the illustrated embodiments without departure from the present invention. Accordingly, it is expressly intended that the foregoing description and accompanying drawings are illustrative of preferred embodiments only, not limiting, and that the true spirit and scope of the present invention will be determined by reference to the appended claims.

What is claimed is:

1. An apparatus for establishing a substantially stable concentration gradient of macro-ions for optical interrogation, said apparatus comprising:

means defining at least one interrogation chamber for confining a volume of macro-ions to be interrogated and a solvent, said interrogation chamber defined by at least one semipermeable membrane adjacent to the confined volume of macro-ions and solvent and having respective optical energy entry and exit ports;

means for directing optical energy through said optical energy entry port, through said confined volume, and through said optical energy exit port;

means for establishing a directed electrical field substantially normal to the surface of said at least one semipermeable membrance to at least cause a concentration gradient of macro-ions within said interrogation chamber and adjacent to said semi-permeable membrane in which opposing forces of diffusion and said directed electrical field define a substantially stabilized concentration gradient of said macro-ions;

means for mouting said at least one interrogation chamber so that the surface of said semipermeable membrane is aligned substantially normal to gravity, said mounting means comprising first and second solvent chambers for containing respective volumes of solvent in communication with each other through said semipermeable membrane and said interrogation chamber, said solvent in communication with each other through said semipermeable membrane and said interrogation chamber, said solvent chambers constituting elements of the said means for establishing a directed electrical field;

first and second electrode means positioned in said first and second solvent chambers for defining an electrical current path between said first and second electrode means via said first and second solvent chambers, said semipermeable membrane, and said interrogation chamber;

a first partition having a restricted area opening dividing said first solvent chamber into a first outer chamber containing said first electrode means an an upper chamber positioned above and in direct communication with said interrogation chamber defining means, whereby said first outer chamber and said upper chamber are in fluid communication through said first restricted area opening; and a second partition having a restricted area opening dividing said second solvent chamber into a second outer chamber containing said second electrode means and a lower chamber positioned below and in direct communication with said interrogation chamber defining means, whereby said second outer chamber and said lower chamber are in fluid communication thorugh said first restricted area opening.

2. An apparatus for establishing a substantially stable concentration gradient of macro-ions for optical interrogation, said apparatus comprising:

means defining a first interrogation chamber for confining a volume of macro-ions to be interrogated and a solvent, said first interrogation chamber comprising at least one semipermeable membrane adjacent to the confined volume of macro-ions and solvent and respective first optical energy entry and exit ports;

means defining a second interrogation chamber for confining a volume of solvent, said second interrogation chamber comprising respective second optical energy entry and exit ports;

means for directing optical energy through said first and second confined volumes, and through said first and second optical energy exit ports;

means for establishing a directed electrical field substantially normal to the surface of said at least one semipermeable membrane to at least cause a concentration gradient of macro-ions within said first interrogation chamber and adjacent to said at least one semipermeable membrane in which opposing forces of diffusion and said directed electrical field define a substantially stabilized concentration gradient of said macro-ions;

means for mounting said first and second interrogation chambers so that the surface of said at least one semipermeable membrane is aligned substantially normal to gravity, said mounting means comprising first and second solvent chambers for containing respective volumes of solvent in communication with each other through said at least one semipermeable membrane and said first interrogation chamber, said first and second solvent chambers constituting elements of the said means for establishing a directed electrical field;

first and second solvent chambers contain respective first and second electrode means positioned in said first and second solvent chambers for defining an electrical current path between said first and second electrode means via said first and second solvent chambers, said semipermeable membrane, and said first interrogation chamber;

a first partition having a restricted area opening dividing said first solvent chamber into a first outer chamber containing said first electrode means and an upper chamber positioned above and in direct communication with said first interrogation chamber defining means, whereby said first outer chamber and said upper chamber are in fluid communication through said first restricted area opening; and a second partition having a restricted area opening dividing said second solvent chamber into a second outer chamber containing said second electrode means and a lower chamber positioned below and in direct communication with said first interrogation chamber defining means, whereby said second outer chamber and said lower chamber are in fluid communication through said second restricted area opening.

3. A method for optically interrogating-macro-ions established in a substantially stable concentration gradient, said method comprising the steps of:

confining a solution of macro-ions and a solvent to a selected volume adjacent to at least one semipermeable membrane;

establishing a directed electrical field substantially normal to the surface of said semipermeable membrane to at least cause a concentration gradient of said macro-ions adjacent to said semipermeable membrane in which opposing forces of diffusion and said directed electrical field define a substantially stabilized concentration gradient of said macro-ions;

passing a first beam of optical energy through said selected volume, said first beam of optical energy affected by said concentration gradient of macro-ions as a function of at least one property of said macro-ions;

passing a second beam of optical energy substantially parallel to said first beam of optical energy; and detecting said first beam of optical energy after passage through said selected volume and detecting said second beam of optical energy.

4. The method of claim 3 for optically interrogating macro-ions established in a substantially stable concentration gradient, said method further comprising the step of:

measuring the intensity of said first beam of optical energy after passage through said selected volume as a function of the absorbance of said macro-ions.

5. The method of claim 3 for optically interrogating macro-ions established in a substantially stable concentration gradient, said method further comprising the step of:

comparing said first beam of optical energy after passage through said selected volume with said second beam of optical energy to form an interferogram.

6. The method of claim 4 for optically interrogating macro-ions established in a substantially stable concentration gradient, said method further comprising the step of:

comparing the intensity of said first beam of optical energy after passage through said selected volume with the intensity of said second beam of optical energy as a function of the absorbance of said macro-ions.

7. A method for optically interrogating macroions established in a substantially stable concentration gradient, said method comprising the steps of:

confining a solution of macro-ions and a solvent to a first selected volume adjacent to a semipermeable membrane;

confining a solution of a solvent to a second selected volume adjacent to said first selected volume;

establishing a directed electrical field substantially normal to the surface of said semipermeable membrane to at least cause a concentration gradient of said macro-ions adjacent to said semipermeable membrane in which opposing forces of diffusion and said directed electrical field define a substantially stabilized concentration gradient of said macro-ions;

passing a first beam of optical energy through said first selected vlume, said first beam of optical energy affected by said concentration gradient of macro-ions as a function of at least one property of said macro-ions; and passing a second beam of optical energy substantially parallel to said first beam of optical energy through said second selected volume.

8. The method of claim 7 for optically interrogating macro-ions established in a substantially stable concentration gradient, said method further comprising the step of:

comparing said first and second beams of optical energy after passage through said respective first and second selected volumes to form an interferogram.

9. The method of claim 7 for optically interrogating macro-ions established in a substantially stable concentration gradient, said method further comprising the steps of:

measuring the intensity of said first beam of optical energy after passage through said first selected volume as a function of the absorbance of said macro-ions; and measuring the intensity of said second beam of optical energy after passage through said second selected volume.

10. The method of claim 9 for optically interrogating macro-ions established in a substantially stable concentration gradient, said method further comprising the step of:

comparing the intensities of said first and second beams of optical energy after passage through said respective first and second selected volumes as a function of the absorbance of said macro-ions.

* * * * *

UNITED STATES PATENT AND TRADEMARK OFFICE
CERTIFICATE OF CORRECTION

PATENT NO. : 4,801,366

DATED : January 31, 1989

INVENTOR(S) : GODFREY, Jamie E.

It is certified that error appears in the above-identified patent and that said Letters Patent is hereby corrected as shown below:

IN THE DRAWING

|  | Delete | Substitute |
|---|---|---|
| FIG. 6b | 10 | 100 |
| FIG. 7b | 100 | 101 |

| Col. | Line | Delete | Substitute |
|---|---|---|---|
| 1 | 47 | maintaind | maintained |
| 1 | 58 | -quasi/chemical- | -/quasi-chemical- |
| 4 | 67 | ion | ions |
| 9 | 6 | cndidates | candidates |
| 11 | 10 | elevate | elevated |
| 12 | 52 | I | 1 |
| 14 | 18 | topper | stoppers |
| 15 | 21 | identical, to | identical to |
| 16 | 5 | dimenionally | dimensionally |
| 17 | 12 | 72 70 | 72 of the compound gaskets 70 |

UNITED STATES PATENT AND TRADEMARK OFFICE
CERTIFICATE OF CORRECTION

PATENT NO. : 4,801,366

DATED : January 31, 1989

INVENTOR(S) : GODFREY, Jamie E.

It is certified that error appears in the above-identified patent and that said Letters Patent is hereby corrected as shown below:

| | | | |
|---|---|---|---|
| 18 | 58 | 59'', and 59'' | 59'' and, 59''' |
| 21 | 27 | assemblage( | assemblage, |
| 21 | 63 | cell fitted | cells fitted |
| 22 | 46 | are | is |
| 23 | 18-19 | toppers | stoppers |
| 24 | 9 | FIG. 12a | FIG. 3a |
| 25 | 4 | ppropriate | appropriate |
| 25 | 26 | 11 | 115 |
| 25 | 58 | 130 | 130 |
| 26 | 5 | 113b | 113b |
| 27 | 47 | 100 | 101 |
| 29 | 17 | macroions | macro-ions |
| 29 | 27 | 6Ia | 61a |
| 31 | 16 | 6a | 61a |
| 31 | 22 | F's | $\bar{F}$'s |
| 31 | 35-40 | $\partial \mu / \partial x$ | $\partial \bar{\mu} / \partial x$ |
| 31 | 40-45 | $\partial X / \partial x$ | $\partial \psi / \partial x$ |
| 31 | 40-45 | $F_j$ | $\bar{F}_j$ |
| 31 | 45 | $C_m$ | $C_m$ |
| 31 | 46 | 112, $\mathbf{f}$m | 112, $\mathbf{f}$m |
| 31 | 52 | $\partial \omega / \partial x$ | $\partial \psi / \partial x$ |

UNITED STATES PATENT AND TRADEMARK OFFICE
CERTIFICATE OF CORRECTION

PATENT NO. : 4,801,366

DATED : January 31, 1989

INVENTOR(S) : GODFREY, Jamie E.

It is certified that error appears in the above-identified patent and that said Letters Patent is hereby corrected as shown below:

| Col | Line | From | To |
|---|---|---|---|
| 31 | 54 | $c_m/NA^{fm}$ | $c_m/NA^{fm}$ |
| 31 | 55 | $Fz_m(\partial\omega/\partial x)$ | $Fz_m(\partial\psi/\partial x)$ |
| 31 | 56 | $-\partial\omega/\partial x$ | $-\partial\psi/\partial x$ |
| 32 | 20-25 | $\partial X/\partial x$ | $\partial\psi/\partial x$ |
| 32 | 53 | $\partial\omega/\partial x$ | $\partial\psi/\partial x$ |
| 33 | 15 | 1I2 | 112 |
| 33 | 25-30 | $(dc_m/dx) +$ | $(dc_m/dx) =$ |
| 33 | 32 | ym | $Y_m$ |
| 33 | 37 | $\partial\omega/\partial x$ | $\partial\psi/\partial x$ |
| 33 | 40 | $\partial X/\partial x$ | $\partial\psi/\partial x$ |
| 33 | 59 | Phvsical | Physical |
| 34 | 7 | $X(\kappa Rm)$ | $X(\kappa R_m)$ |
| 34 | 10-15 | $N_a$ | $N_A$ |
| 34 | 36 | $dc_m/c_m dx$ | $dc_m/(c_m dx)$ |
| 35 | 42 | 1I2 | 112 |
| 35 | 45-50 | B' | 2B' |
| 35 | 51 | $(x_s - x)$ | $(x - x_s)$ |
| 35 | 51 | B' | 2B' |
| 35 | 51 | $(c_{ms} - c_m)$ | $(c_m - c_{ms})$ |
| 35 | 65 | $(x_s - x)$ | $(x - x_s)$ |
| 35 | 65 | B' | 2B' |

UNITED STATES PATENT AND TRADEMARK OFFICE
CERTIFICATE OF CORRECTION

PATENT NO. : 4,801,366

DATED : January 31, 1989

INVENTOR(S) : GODFREY, Jamie E.

It is certified that error appears in the above-identified patent and that said Letters Patent is hereby corrected as shown below:

| | | | |
|---|---|---|---|
| 35 | 65 | $(c_{is} - c_i)$ | $(c_i - c_{is})$ |
| 36 | 10-15 | $\int_a$ | $\int$ |
| 36 | 28 | $(Fz'_i/Fz'_1) \ln y_1$ | $(Fz'i/Fz'1) \ln y_1$ |
| 36 | 67-68 | Introdction | Introduction |
| 37 | 33 | many self- | many reversibly self- |
| 37 | 64 | molecularweight | molecular-weight |
| 39 | 38 | 66,. | 66. |
| 41 | 13 | $d(\ln c)$ | $d(\ln c_m)$ |
| 41 | 14 | (equation 11) | equation 17 |
| 41 | 41 | I | 1 |
| 41 | 58 | turnaroud . | turnaround |
| 42 | 15 | block-embodiment | block-component-embodiment |
| 42 | 28 | $d(\ln c_m)dx)$ | $d(\ln c_m)dx$ |
| 43 | 47 | block-compound | block-component |
| 43 | 66 | oithe | of the |
| 44 | 28 | I06b | 106b |
| 45 | 3 | oell-block | cell-block |
| 45 | 65 | I | 1 |

UNITED STATES PATENT AND TRADEMARK OFFICE
CERTIFICATE OF CORRECTION

PATENT NO. : 4,801,366

DATED : January 31, 1989

INVENTOR(S) : GODFREY, Jamie E.

It is certified that error appears in the above-identified patent and that said Letters Patent is hereby corrected as shown below:

| | | | |
|---|---|---|---|
| 46 | 4-5 | macr-oion | macro-ion |
| 47 | 17 | 113b | 113b |
| 48 | 39 | dualbeam | dual-beam |
| 48 | 42 | upperand | upper- and |
| 48 | 43 | blockcomponent | block-component |
| 50 | 23 | absence | absence of |

IN THE CLAIMS

| Col. | Line | Delete | Substitute |
|---|---|---|---|
| 51 | 55 | membrance | membrane |
| 51 | 62 | mouting | mounting |
| 51 | 1-3 | said solvent in communication with each other through said semi-permeable membrane and said interrogation chamber, | |
| 52 | 23 | an an | and an |
| 53 | 7 | first and second | said first and second |
| 53 | 7 | contain | containing |

UNITED STATES PATENT AND TRADEMARK OFFICE
CERTIFICATE OF CORRECTION

PATENT NO. : 4,801,366

DATED : January 31, 1989

INVENTOR(S) : GODFREY, Jamie E.

It is certified that error appears in the above-identified patent and that said Letters Patent is hereby corrected as shown below:

| | | | |
|---|---|---|---|
| 53 | 34 | interrogating-macro | interrogating macro |
| 54 | 16 | macroions | macro-ions |
| 54 | 33 | vlume | volume |

Signed and Sealed this

Fourteenth Day of January, 1992

Attest:

HARRY F. MANBECK, JR.

*Attesting Officer*  *Commissioner of Patents and Trademarks*